US007371780B2

(12) United States Patent
Parissenti

(10) Patent No.: US 7,371,780 B2
(45) Date of Patent: May 13, 2008

(54) USE OF CALPHOSTIN C TO TREAT DRUG-RESISTANT TUMOR CELLS

(76) Inventor: Amadeo Parissenti, c/o Northeastern Ontario Regional Cancer Ctr., 41 Ramsey Lake Road, Sudbury, Ontario (CA) P3E 5J1

( * ) Notice: Subject to any disclaimer, the term of this patent is extended or adjusted under 35 U.S.C. 154(b) by 182 days.

(21) Appl. No.: 10/974,310

(22) Filed: Oct. 27, 2004

(65) Prior Publication Data

US 2005/0113320 A1 May 26, 2005

Related U.S. Application Data

(60) Provisional application No. 60/519,057, filed on Nov. 11, 2003.

(51) Int. Cl.
*A61K 31/21* (2006.01)
(52) U.S. Cl. ...................................... 514/510
(58) Field of Classification Search ............... None
See application file for complete search history.

(56) References Cited

U.S. PATENT DOCUMENTS 5,972,598 A * 10/1999 Chaudhary et al. ............ 435/6

FOREIGN PATENT DOCUMENTS

WO    WO 94/04541    3/1994

OTHER PUBLICATIONS

Sausville et al. Contributions of human tumor xenografts to anti-cancer drug development. Cancer Research, 2006, vol. 66, pp. 3351-3354.*

Johnson et al. Relationships between drug activity in NCI preclinical in vitro and in vivo models and early clinical trials. British J. of Cancer, 2001, 84(10):1424-1431.*

Avendano C, Menendez JC: Inhibitors of Multidrug Resistance to Antitumor Agents (MDR). Curr. Med. Chem. 9, 159-193, 2002.

Fukuda T, Kamishima T, Kakihara T, Ohnishi Y, Suzuki T: Characterization of Newly Established Human Myeloid Leukemia Cell Line (KF-19) and its Drug Resistant Sublines. Leuk. Res. Vol. 20, No. 11/12, 931-939, 1996.

Boesch D, Muller K, Pourtier-Manzanedo A, Loor F: Restoration of Daunomycin Retention in Multidrug-Resistant P388 Cells by Submicromolar Concentrations of SDZ PSC 833, a Nonimmunosuppressive Cyclosporin Derivative. Exp. Cell Res. 196, 26-32, 1991.

Boesch D, Gaveriaux C, Jachez B, Pourtier Manzanedo A, Bollinger P, Loor F: In Vivo Circumvention of P-Glycoprotein-mediated Multidrug Resistance of Tumor Cells with SDZ PSC 833. Cancer Res. 51, 4226-4233, 1991.

(Continued)

*Primary Examiner*—Ardin H. Marschel
*Assistant Examiner*—James D. Anderson
(74) *Attorney, Agent, or Firm*—Brinks Hofer Gilson & Lione

(57) ABSTRACT

Calphostin C is used to treat subjects for cancer which is resistant to treatment by other forms of chemotherapeutic drugs, for example breast or uterine cancer, or other cancers characterized by tumor cells that have a defect in an apoptotic regulatory pathway which renders said cells resistant to at least some other forms of chemotherapeutic treatment. The other chemotherapeutic drug used with calphostin C is selected from the group comprising taxanes and anthracyclines, such as paclitaxel or doxorubicin. The use may take the form of administering calphostin C and then subjecting the patient to photodynamic therapy (PDT).

17 Claims, 9 Drawing Sheets

OTHER PUBLICATIONS

Efferth T, Fabry U, Osieka R: Apoptosis and resistance to daunorubicin in human leukemic cells. Leukemia 11, 1180-1186, 1997.

Sikic BI.: Modulation of Multidrug Resistance: A Paradigm for Translational Clinical Research. Oncology vol. 13, 183-187, 1999.

Ogretmen B, Safa AR: Down-regulation of apoptosis-related bcl-2 but not bcl-xL or bax proteins in multidrug resistant MCF-7/Adr human breast cancer cells. Int. J. Cancer 67, 608-614, 1996.

Ikemoto H, Tani E, Matsumoto T, Nakano A, Furuyama J: Apoptosis of human glioma cells in response to calphostin C, a specific protein kinase C inhibitor. J. Neurosurg vol. 83, 1008-1016, 1995.

Zhu DM, Narla RK, Fang WH, Chia NC, Uckun FM: Calphostin C Triggers Calcium-Dependent Apoptosis in Human Acute Lymphoblastic Leukemia Cells. Clin. Cancer Res. Vol. 4, 2967-2976, 1998.

Jarvis WD, Turner AJ, Povirk LF, Traylor RS, Grant S: Induction of Apoptotic DNA Fragmentation and Cell Death in HL-60 Human Promyelocytic Leukemia Cells Pharmacological Inhibitors of Protein Kinase C. Cancer Res. 54, 1707-1714, 1994.

Ikemoto H, Tani E, Ozaki I, Kitagawa H, Arita N: Calphostin C-mediated translocation and Integration of Bax into mitochondria induces cytochrome c release before mitochondrial dysfunction. Cell Death Differ. 7, 511-520, 2000.

LaRue JM, Stratagoules ED, Martinez JD: Deoxycholic acid-induced apoptosis is switched to necrosis by bcl-2 and calphostin C. Cancer Lett. 152, 107-113, 2000.

Pollack IF, Kawecki S: The effect of calphostin C, a potent photodependent protein kinase C inhibitor, on the proliferation of glioma cells in vitro. J. of Neuro-Oncology 31, 255-266, 1997.

Hu DE, Fan TP: Protein kinase C Inhibitor calphostin C prevents cytokine-induced angiogenesis in the rat. Inflammation vol. 19, No. 1, 39-54, 1995.

Chen CL, Tai HL, Zhu DM, Uckun FM: Pharmacokinetic Features and Metabolism of Calphostin C, A Naturally Occurring Perylenequinone with Antileukemic Activity. Pharm. Res. vol. 16, No. 7 1003-1009, 1999.

da Rocha AB, Mans DR, Regner A, Schwartsmann G: Targeting Protein Kinase C: New Therapeutic Opportunities Against High-Grade Malignant Gliomas? The Oncologist 7, 17-33, 2002.

Traci P. Beck, Edward J. Kirsh, Steven J. Chmura, David A. Kovar, Theodore Chung, Carrie W. Rinker-Schaeffer, Walter M. Stadler; In Vitro Evaluation of Calphostin C as a Novel Agent for Photodynamic Therapy of Bladder Cancer; Basic Science Elsevier Science Inc.; Apr. 16, 1999; 573-577.

Zita Dubauskas, Traci P. Beck, Steven J. Chmura, David A. Kovar, Mithra M. Kadkhodaian, Maneesh Shrivastav, Theodore Chung, Walter M. Stadler, Carrie W. Rinker-Schaeffer; Activated Calphostin C Cytotoxicity is Independent of p53 Status and in Vivo Metastatic Potential; Clinicai Cancer Research; Oct. 1998; vol. 4, 2391-2398.

Sudhir Gupta, Keyur Patel, Harpreet Singh, Sastry Gollapudi; Effect of Calphostin C (PKC inhibitor) on Daunorubicin Resistance in P388/ADR and HL60/AR Cells: Reversal of Drug Resistance Possibly Via P-glycoprotein; Cancer Letters 76 Elsevier Scientific Publishers Ireland; 1994; 139-145.

Eiji Kobayashi, Katsuhiko Ando, Hirofumi Nakano, Takao Iida, Hiroe Ohno, Makoto Morimoto, Tatsuya Tamaoki; Calphostins (UCN-1028), Novel and Specific Inhibitors of Protein Kinase C I. Fermentation, Isolation, Physico-Chemical Properties and Biological Activities; The Journal of Antibiotics; Oct. 1989; 1470-1474.

Sabina Sperandio, Ian de Belle, Dale E. Bredesen; An Alternative, Nonapoptotic Form of Programmed Cell Death; PNAS Dec. 19, 2000; vol. 97, No. 26; 14376-14381.

Suresh V. Ambudkar, Saibal Dey, Christine A. Hrycyna, Muralidhara Ramachandra, Ira Pastan, Michael M. Gottesman; Biochemical, Cellular, and Pharmacological Aspects of the Multidrug Transporter; 1999; 39:361-98; Annu. Rev Pharmacol. Toxicol.

Susan E. Bates, Jong Seok Lee, Bruce Dickstein, Mary Spolyar, Antonio T. Fojo; Differential Modulation of P-Glycoprotein Transport by Protein Kinase Inhibition; May 21, 1993; 32, 9156-9164; Biochemistry 1993 American Chemical Society.

April L. Blajeski, Timothy J. Kottke, Scott H. Kaufmann; A Multistep Model for Paclitaxel-Induced Apoptosis in Human Breast Cancer Cell Lines; 2001; 277-288; Experimental Cell Research Academic Press.

Antony Chadderton, David J. Villeneuve, Stefan Gluck, Angie F. Kirwan-Rhude, Brian R. Gannon, David E. Blais, Amadeo M. Parissenti; Role of Specific Apoptotic Pathways in the Restoration of Paclitaxel-Induced Apoptosis by Valspodar in Doxorubicin-Resistant MCF-7 Breast Cancer Cells; 2000; 59:231-244; Breast Caner Research and Treatment Kluwer Academic Publishers.

Ann-Lii Cheng, Shuang-En Chuang, Robert L. Fine, Kun-Huei Yeh, Chao-Ming Liao, Jong-Ding Lay, Ding-Shinn Chen; Inhibition of the Membrane Translocation and Activation of Protein Kinase C, and Potentiation of Doxorubicin-Induced Apoptosis of Hepatocellular Carcinoma Cells by Tamoxifen; 1998; vol. 55 pp. 523-531; Biochemical Pharmacology Elsevier Science.

Sarah Childs, Victor Ling; the MDR Superfamily of Genes and Its Biological Implications; 1994; 21-36; Important Advances in Oncology Lippincott Company, Philadelphia.

Amy S. Clark, Kip A. West, Peter M. Blumberg, Phillip A. Dennis; Altered Protein Kinase C (PKC) Isoforms in Non-Small Cell Lung Cancer Cells: PKCδ Promotes Cellular Survival and Chemotherapeutic Resistance; Feb. 15, 2003; 63, 780-786; Cancer Research Advances in Brief.

S. P. C. Cole, G. Bhardwaj, J. H. Gerlach, J. E. Mackie, C. E. Grant, K. C. Almquist, A. J. Stewart, E. U. Kurz, A. M. V. Duncan, R. G. Deeley; Overexpression of a Transporter Gene in a Multidrug-Resistant Human Lung Cancer Cell Line; Dec. 4, 1992; vol. 258, 1650-1654; Science.

Gwenaëlle Conseil, Joseé Maria Perez-Victoria, Jean-Michel, Francisco Gamarro, André Goffeau, Johann Hofmann, Attilio Di Pietro; Protein Kinase C Effectors Bind to Multidrug ABC Transporters and Inhibit Their Activity; Dec. 13, 2000, 2001; 40, 2564-2571; American Chemical Society.

John Crown; Nonanthracycline Containing Docetaxel-Based Combinations in Metastatic Breast Cancer; Mar. 5, 2001; 2001, 6(suppl 3) 17-21; The Oncologist.

Christina P. da Silva, Catarina R. de Oliveira, Maria da Conceição P. de Lima; Apoptosis as a Mechanism of Cell Death Induced by Different Chemotherapeutic Drugs in Human Leukemic T-Lymphocytes; 1996 vol. 51 pp. 1331-1340; Biochemical Pharmacology, Elsevier Science, Inc.

Tony Elliott, Tariq Sethi; Integrins and Extracellular Matrix: A Novel Mechanism of Multidrug Resistance; 2002 449-459; Expert Rev. Anticancer Ther. 2(4), Future Drugs ltd.

George A. Fisher, MD, PhD, Branimir I. Sikic, MD; Clinical Studies With Modulators of Multidrug Resistance; Apr. 1995; vol. 9 pp. 363-382; Drug Resistance in Clinical Oncology and Hematology, Hematology/Oncology Clinics of North America Stanford University School of Medicine.

Antoni Fojo, Shin-ichi Akyama, Michael M. Gottesman, Ira Pastan; Reduced Drug Accumulation in Multiply Drug-Resistant Human KB Carcinoma Cell Lines; Jun. 1985; 45, 3002-3007; Cancer Research, Laboratory of Molecular Biology, National Cancer Institute, National Institutes of Health, Bethesda, Maryland.

Katrin Friedrich, Thomas Vieder, Clarissa Von Haefen, Silke Radetzki, Reiner Jänicke, Klaus Schulze-Osthoff, Bernd Dörken, Peter T. Daniel; Overexpression of Caspase-3 Restores Sensitivity for Drug-Induced Apoptosis in Breast Cancer Cell Lines With Acquired Drug Resistance; Feb. 6, 2001; 20, 2749-2760; Oncogene (2001).

C. Friesen, S. Fulda, K-M Debatin; Deficient Activation of the CD95 (APO-1Fas) System in Drug-Resistant Cells; Jul. 8, 1997; 11, 1833-1841; Leukemia (1997) Hematology/Oncology, University Children's Hospital Prittwitzstr, Germany.

Andrew M. Fry, Christine M. Chresta, Stella M. Davies, M. Claire Walker, Adrian L. Harris, John A. Hartley, John R. W. Masters, Ian D. Hickson; Relationship Between Topoisomerase II Level and Chemosensitivity in Human Tumor Cell Lines; Dec. 15, 1991; 51, 6592-6595; Cancer Research.

Jianxin Fu, Zixing Chen, Jiannong Chen, Changgeng Ruan; Expression of the Human Multidrug Resistance Gene mdr1 in Leukemic Cells and its Application in Studying P-Glycoprotein Antagonists; 2000; 113.3 pp. 228-231; Chinese Medical Journal.

Giuseppe Giaccone, Adi F. Gazdar, Hans Beck, Franco Zunino, Giovanni Capranico; Multidrug Sensitivity Phenotype of Human Lung Cancer Cells Associated with Topoisomerase II Expression; Apr. 1, 1992; 52, 1666-1674; Cancer Research.

U. A. Germann; P-Glycoprotein-A Mediator of Multidrug Resistance in Tumor Cells; 1996; vol. 32A, No. 6, pp. 927-944; European Journal of Cancer.

Michael M. Gottesman, Tito Fojo, Susan E. Bates; Multidrug Resistance in Cancer: Role of ATP-Dependent Transporters; Jan. 2002; Vol. 2, pp. 48-58; www.nature.com/reviews/cancer Nature Reviews/Cancer.

Adrian L. Harris, Daniel Hochhauser; Mechanisms of Multidrug Resistance in Cancer Treatment; Aug. 21, 1991; vol. 31, No. 2, pp. 205-213; Aeta Oncologica (1992).

Susan Band Horwitz; Mechanism of Action of Taxol; Apr. 1992; vol. 13 pp. 134-136; TiPS -Elsevier Science Publishers Ltd (UK).

Hideyasu Ikemoto, M.D., Eiichi Tani, M.D., Tsuyoshi Matsumoto, M.D., Atsushisa Nakano, M.D., Jun-ichi Furyama, Ph.D.; Apoptosis of Human Glioma Cells in Response to Calphostin C, a Specific Protein Kinase C Inhibitor; Jun. 6, 1995; vol. 83, pp. 1008-1016; J Neurosurg (Dec. 1995).

H. Ikemoto, E. Tani, I Ozaki, H. Hitagawa, N. Arita; Calphostin C-Mediated Translocation and Integration of Bax into Mitochondria Induces Cytochrome C Release Before Mitochondrial Dysfunction; Feb. 15, 2000; vol. 7, pp. 511-520; Cell Death and Differentiation, www.nature.com/cdd.

Reiner U. Jäanicke, Michael L. Sprengart, Mas R. Wati, Alan G. Porter; Caspace-3 is Required for DNA Fragmentation and Morphological Changes Associated with Apoptosis; Feb. 6, 1998; vol. 273, No. 16 pp. 9357-9360; The Journal of Biological Chemistry.

Reiner U. Jänicke, Patrick Ng, Michael L. Sprengart, Alan G. Porter; Caspase-3 is Required for α-Fodrin Cleavage but Dispensable for Cleavage of Other Death Substrates in Apoptosis; Jun. 19, 1998; vol. 273, No. 25 pp. 15540-15545; The Journal of Biological Chemistry.

W. David Jarvis, Amy J. Turner, Lawrence F. Povirk, Rebecca S. Traylor, Steven Grant; Induction of Apoptotic DNA Fragmentation and Cell Death in HL-60 Human Promyelocytic Leukemia Cells by Pharmacological Inhibitors of Protein Kinase C[1]; Apr. 1, 1994; vol. 54 pp. 1707-1714; Cancer Research.

Mary Ann Jordan, Robert J. Toso, Doug Thrower, Leslie Wilson; Mechanism of Mitotic Block and Inhibition of Cell Proliferation by Taxol at Low Concentrations; Oct. 1993; vol. 90 pp. 9552-9556; Proc. Natl. Acad. Sci. USA.

Mary Ann Jordan, Kim Wendell, Sara Gardiner, W. Brent Derry, Hillary Copp, Leslie Wilson; Mitotic Block Induced in HeLa Cells by Low Concentrations of Paclitaxel (Taxol) Results in Abnormal Mitotic Exit and Apoptotic Cell Death[1]; Feb. 15, 1996; 56 pp. 816-825; Cancer Research.

Reinhold Kerb, Sven Hoffmeyer, Ulrich Brinkmann; ABC Drug Transporters: Hereditary Polymorphisms and Pharmacological Impact in MDR1, MRP1 and MRP2; 2001 2(1) pp. 51-64; Epidauros Biotechnology, Pharmacogenetics Laboratory, Bernried, Germany Ashley Publications Ltd. www.ashley-pub.com.

Zhen-Li Liu, Kenji Onda, Sachiko Tanaka, Tsugutoshi Toma, Toshihiko Hirano, Kitaro Oka; Induction of Multidrug Resistance in Molt-4 Cells by Anticancer Agents is Closely Related to Increased Expression of Functional P-Glycoprotein and MDR1 mRNA; Pub Online Feb. 14, 2002; 49 pp. 391-397; Cancer Chemother Pharmacol.

A. N. Makarovskiy, E. Siryaporn, D.C. Hixson, W. Akerley; Reasearch Article Survival of Docetaxel-Resistant Prostate Cancer Cells In Vitro Depends on Phenotype Alterations and Continuity of Drug Exposure; May 27, 2002; 59, pp. 1198-1211; CMLS Cellular and Molecular Life Sciences.

Tsuyoshi Matsumoto, M.D., Eiich Tani, M.D., Ikuya Yamaura, M.D., Keizo Kaba, M.D.; Effects of Protein Kinase C Modulators on Multidrug Resistance in Human Glioma Cells; Mar. 3, 1995; vol. 36, No. 36 pp. 565-572; Experimental Studies Neurosurgery.

Jeffery W. Pollard, John M. Walker; Animal Cell Culture; Ch 27 pp. 331-337; Methods in Molecular Biology 5.

Alison M. G. Robertson, C. C. Bird, A. W. Waddell, A. R. Currie; Morphological Aspects of Glucocorticoid-Induced Cell Death in Human Lymphoblas-Toid Cells (Plates LI-LV); May 3, 1978; vol. 126 (1978) pp. 181-187; J. Path.

Igor B Roninson; Molecular and Cellular Biology of Multidrug Resistance in Tumor Cells; 1991;Contents ix-xviii.

Douglas D. Ross, Weidong Yang, Lynne V. Abruzzo, William S. Dalton, Erasmus Schneider, Hermann Lage, Manfred Dietel, Lee Greenberger, Susan P.C. Cole, L. Austin Doyle; Atypical Multidrug Resistance: Breast Cancer Resistance Protein Messenger RNA Expression in Mitoxantrone-Selected Cell Lines; Mar. 3, 1999; vol. 91, No. 5 pp. 429-433; Accelerated Discovery Journal of the National Cancer Institute.

Benjamin Tan, MD, David Piwnica-Worms, MD, PhD, Lee Ratner, MD, PhD; Multidrug Resistance Transporter and Modulation; 2000; pp. 450-458; Current Opinion in Oncology Cancer in AIDS.

Dwight E. Saunders, W. Dwayne Lawrence, Carl Christensen, Nanci L. Wappler, Hangming Ruan, Gunter Deppe; Paclitaxel-Induced Apoptosis in MCF-7 Breast-Cancer Cells; Oct. 9, 1996; 70, pp. 214-220 (1997); Publication of the International Union Against Cancer.

George L. Scheffer, Peter L.J. Wijngaard, Marcell J. Flens, Miguel A. Izquierdo, Marilyn L. Slovak, Herbert M. Pinedo, Chris J.L.M. Meijer, Hans C. Clevers, Rik J. Scheper; the Drug Resistance-Related Protein LRP is the Human Major Vault Protein; Jun. 1995; vol. 1 No. 6 pp. 578-582; Nature Medicine Articles.

Annalucia Serafino, Paola Sinibaldi-Vallebona, Pasquale Pierimarchi, Paola Bernard, Giorgio Gaudiano, Claudia Massa, Guido Rasi, Giampietro Ranagnan; Induction of Apoptosis in Neoplastic Cells by Anthracycline Antitumor Drugs: Nuclear and Cytoplasmic Triggering?; 1999; 19, pp. 1909-1918; Anticancer Research.

Jennifer A. Shabbits, Rajesh Krishna, Lawrence D. Mayer; Molecular and Pharmacological Strategies to Overcome Multidrug Resistance; 2001; 1(4) pp. 585-594; Future Drugs Ltd.

J. W. Sheridan, C. J. Bishop, R. J. Simmons; Biophysical and Morphological Correlates of Kinetic Change and Death in a Starved Human Melanoma Cell Line; 1981; 49, pp. 119-137; J. Cell Sci. Printed in Great Britian.

Branimir I. Sikic; Editorial—Modulation of Multidrug Resistance: at the Threshold; Sep. 1993; vol. 11 No. 9, pp. 1629-1635; Journal of Clinical Oncology.

Xiao-Ming Sun, Marion MacFarlane, Jianguo Zhuang, Beni B. Wolf, Douglas R. Green, Gerald M. Cohen; Distinct Caspase Cascades are Initiated in Receptor-Mediated and Chemical-Induced Apoptosis; Feb. 19, 1999; vol. 274 No. 8 pp. 5053-5060; The Journal of Biological Chemistry.

Kohji Takara, Toshiyuki Sakaeda, Tatsurou Yagami, Hironao Kobayashi, Nobuko Ohmoto, Masanori Horinouchi, Kohshi Nishiguchi, Katsuhiko Okumura; Cytoxic Effects of 27 Anticancer Drugs in HeLa and MDR1-Overexpressing Derivative Cell Lines; Jun. 2002; 25(6) pp. 771-778; Biol. Pharm. Bull. Pharmaceutical Society of Japan.

Marieze Tarr, Paul D. van Helden; Inhibition of Transcription by Adriamycin is a Consequence of the Loss of Negative Superhelicity in DNA Mediated by Topoisomerase II; Jul. 17, 1989; 93 pp. 141-146; Molecular and Cellular Biochemistry (1990).

Takashi Tsuruo, Mikihiko Naito, Akihiro Tomida, Naoya Fujita, Tetsuo Mashima, Hiroshi Sakamoto, Naomi Haga; Molecular Targeting Therapy of Cancer: Drug Resistance, Apoptosis and Survival Signal; Oct. 23, 2002, vol. 94, No. 1 pp. 15-21; Review Article Cancer Sci.

Douglas H. Weitzel, Dale D. Vandré; Differential Spindle Assemble Checkpoint Response in Human Lung Adenocarcinoma Cells; Published online Mar. 7, 2000, 300, pp. 57-65; Cell Tissue Res—Regular Article.

Sebastian Wesselborg, Ingo H. Engels, Evi Rossman, Marek Los, Klaus Schulze-Osthoff; Anticancer Drugs Induce Caspase-8/FLICE Activation and Apoptosis in the Absence of CD95 Receptor/Ligand Interaction; 1999 (May 1), vol. 93, No. 9, pp. 3053-3063; The American Society of Hematology Blood.

Anne-Marie C. Yvon, Patricia Wadsworth, Mary Ann Jordan; Taxol Suppresses Dynamics of Individual Microtubules in Living Human Tumor Cells; Apr. 1999, vol. 10, pp. 947-959; Molecular Biology of the Cell.

De-Min Zhu, Rama-Krishna Narla, Wei-Hua Fang, Nian-Cherng Chia, Fatih M. Uckun; Calphostin C Triggers Calcium-Dependent Apoptosis in Human Acute Lymphoblastic Leukemia Cells; Dec. 1998, vol. 4, pp. 2967-2976; Clinical Cancer Research.

* cited by examiner

USE OF CALPHOSTIN C TO TREAT DRUG-RESISTANT TUMOR CELLS

RELATED APPLICATION

This application claims the benefit under Title 35, U.S.C., S.119(e) of U.S. provisional application No. 60/519,057 filed on Nov. 11, 2003.

FIELD OF THE INVENTION

This invention relates to the field of medicinal chemistry and the use of agents to treat drug-sensitive tumor cells, specifically tumor cells that have become resistant to taxane or anthracycline drugs.

BACKGROUND OF THE INVENTION

A variety of in vitro and clinical studies have shown that cancer cells can exhibit resistance to chemotherapeutic drugs, including two drugs commonly used for chemotherapeutic treatment of breast cancer, particularly, paclitaxel and doxorubicin. Moreover, long-term exposure of tumor cells to one chemotherapeutic agent can often result in cross-resistance to a variety of structurally unrelated drugs. This common phenomenon is termed multidrug resistance (MDR) [1, 2]. The development of multidrug resistance in tumor cells is believed to be a major obstacle to the treatment of cancer by chemotherapy. One of the most well characterized mechanisms for multidrug resistance in tumor cells involves the increased expression of a superfamily of ATP-binding cassette (ABC) drug transporters. These include such well known proteins as P-glycoprotein (P-gp or ABCB1), the multidrug resistance proteins MRP1 (ABCC1) and MRP2 (ABCC2), and the breast cancer resistance protein (BCRP or ABCG2) [3-9]. These ABC transporters actively transport a variety of structurally unrelated chemotherapeutic drugs out of the cells or into vesicles, thereby decreasing intracellular drug accumulation and inhibiting drug-induced cytotoxicity [10, 11]. Multidrug resistance can also stem from a variety of additional mechanisms [12, 13] including enhanced expression of glutathione-S-transferase or glutathione peroxidase [14], reduced topoisomerase II expression [15, 16], cell adhesion to extracellular matrix proteins [17] and the inhibition of drug-induced apoptosis [18-20].

Attempts have been made to overcome multidrug resistance by inhibiting the expression of genes involved in this phenomenon [21], or by blocking P-gp function using cyclosporin A [22], valspodar (PSC-833) [23-26], or verapamil [27]. These P-gp inhibitors increase cellular drug accumulation in drug-resistant cells by competing for drug-binding sites on P-gp, allowing less drug to be extruded by the transporter [28-30]. P-gp inhibitors may improve the outcome of chemotherapy for some cancers by enabling drugs to remain in tumor cells where they can exert their cytotoxic effects. However, this approach appears to be drug and/or cell type specific. For example, cyclosporin A was able to inhibit multidrug resistance by disturbing P-gp function in doxorubicin-resistant human myeloid leukemia cells [22], daunorubicin-resistant human T-lymphoblastoid cells [1] and vincristine-resistant K562/MDR leukemia cells [31], while having no effect on the cytotoxicity of 6-mercaptopurine or mitomycin C in HeLa or Hvr100-6 cells selected for resistance to these agents [32]. Similarly, valspodar can completely restore the cytotoxicity and intracellular accumulation of paclitaxel in doxorubicin-resistant NCI-ADR cells while having no effect on 5-fluorouracil cytotoxicity and uptake [33]. In addition, valspodar could only partially restore doxorubicin cytotoxicity in doxorubicin-resistant MCF-7 cells, while fully restoring paclitaxel cytotoxicity in paclitaxel-resistant MCF-7 cells.

Thus, there remains a need to identify other agents that have the potential to kill a variety of drug-resistant tumor cells, particularly breast cancer cells. The mechanism of action of these agents would preferably be in a P-glycoprotein-independent manner. An agent which could kill breast tumor cells resistant to the anthracycline doxorubicin or the taxane paclitaxel (even in P-gp-expressing cells) would be highly desirable, considering that these drugs are widely used in the treatment of breast cancer and approximately half of patients respond to taxanes after anthracycline chemotherapy [34].

Calphostin C, a highly specific photoactivatable inhibitor of phorbol-responsive protein kinase C (PKC) isoforms [35], is one such agent which has shown some promise in killing drug resistant tumor cells including daunorubicin-resistant tumor cells [36]. Calphostin C has also been employed as an agent to treat non-drug resistant MCF-7 breast cancer cells [77]. Cell death induced by calphostin C has been shown to be independent of the p53, pRb and p16 status of the cells, suggesting that the mechanism of cell death caused by this reagent is likely unaffected by common genetic alterations in cancer [37, 38]. However, it was not previously known whether calphostin C would be useful as chemotherapeutic agent for multi-dug resistant tumor cells, in particular breast cancer tumors resistant to taxane or anthracycline drugs.

SUMMARY OF THE INVENTION

It was the surprising discovery of the inventor that calphostin C can be used to treat cancer which is resistant to treatment by other forms of chemotherapeutic drugs, in particular, taxanes such as paclitaxel and anthracycline.

According to another aspect, the cancer treated by calphostin C can be characterized by tumor cells that have a defect in an apoptotic regulatory pathway which renders the cells resistant to at least some other forms of chemotherapeutic treatment. Such cancer may be breast cancer or uterine cancer.

The invention provides in another aspect, for a method of treating cancer in a subject who is resistant to other forms of chemotherapeutic drugs in particular taxanes and anthracyclines, using photodynamic therapy (PDT) which involves administering calphostin C to a subject, exposing tumor-affected parts of the subject to light within a suitable range of wavelengths for activating the calphostin C, while not exposing other parts of the subject to such light wherein calphostin C remains substantially inactivated in other parts of the patient's body where the tumor is not present. Such patients are resistant to either one of the above classes of drugs or, in particular, to both classes. The invention also relates to a use of calphostin C for treatment of this type.

In particular, calphostin C may be used in a fashion similar to the above in which the compound is administered to the subject, followed by directing a highly focused light beam such as a laser at the tumor in a manner known in the art.

The invention provides, in yet another aspect for a method of killing tumorous cells in vitro comprising administering an effective dose of calphostin C and exposing the cells with a light of suitable intensity and wavelength to activate calphostin C. The cells may be selected from the group comprising MCF-7 human breast cancer cell, MDA-MB231 human breast cancer cell, MES-SA human uterine sarcoma cell, human 293T embryonic kidney cell, mouse B16BL6 melanoma cell and Chinese hamster ovary (CHO) cells.

Although calphostin C is presented as the preferred drug of the method according to the invention, it should be noted that analogues or chemical equivalents of calphostin C can also be used to achieve the same goal.

Figure 1:
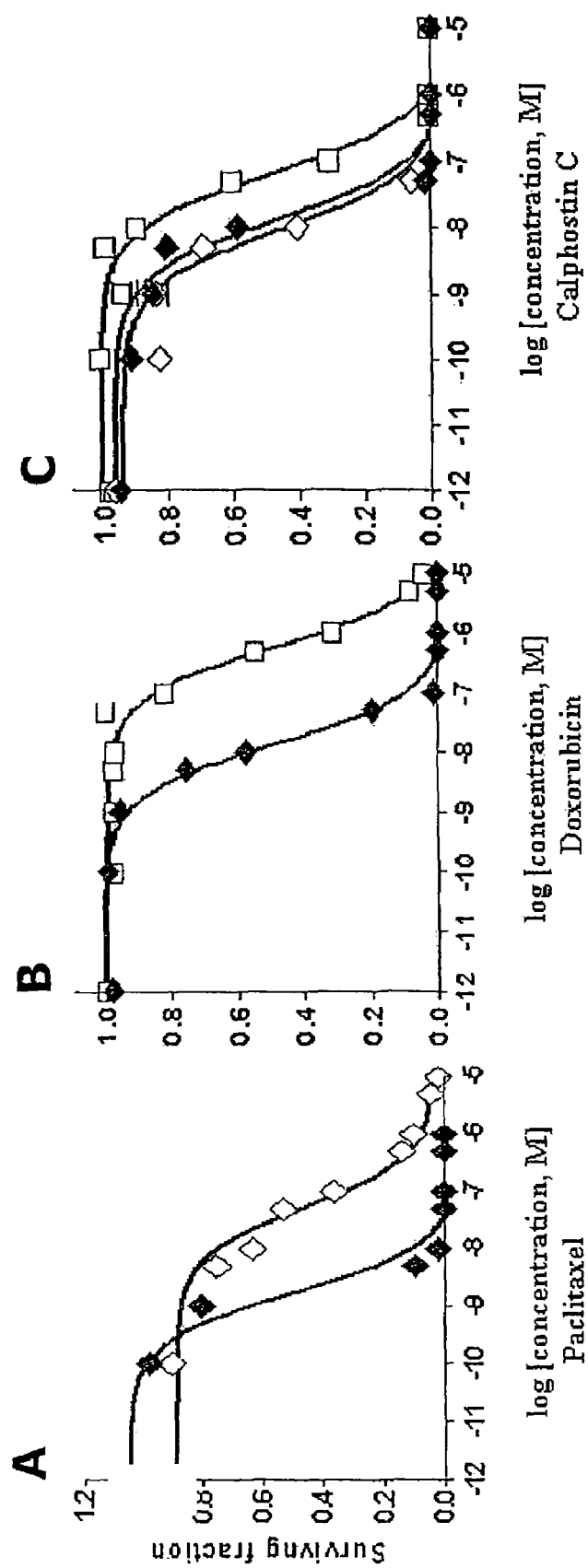
FIG. 1 shows the effect of paclitaxel (A), doxorubicin (B) and calphostin C (C) on the viability of MCF-7 (?), MCF-$7_{TAX}$ (?) and MCF-$7_{DOX}$ (?) cells as measured using a clonogenic assay. Cells treated with calphostin C were exposed to fluorescent light for 2 h. Each data point represents the mean surviving fraction (+/−S.E.) for 5 randomly selected fields in the clonogenic assays. The curves depicted are representative of three independent experiments.

While the invention will be described in conjunction with the illustrated embodiment, it will be understood that it is not intended to limit the invention to such embodiment. On the contrary, it is intended to cover all alternatives, modifications and equivalents as may be included within the spirit and scope of the invention as defined by the appended claims, including elements which are the equivalent to those defined in the claims and which would be recognized as such by persons skilled in the art to which this invention pertains.

DETAILED DESCRIPTION

The invention provides the use of calphostin C to treat subjects for cancer which is resistant to treatment by other forms of chemotherapeutic drugs, in particular taxane or anthracycline drugs.

Such cancer treated by calphostin C can be characterized by tumor cells that have a defect in an apoptotic regulatory pathway which renders the cells resistant to at least some other forms of chemotherapeutic treatment. Such cancer may be breast cancer or uterine cancer. It should be noted that other types of cancer can also be treated by calphostin C according to the invention.

The other forms of chemotherapeutic treatment mentioned above involve taxane and anthracycline drugs, particularly, paclitaxel and doxorubicin.

Materials and Methods

Cell Lines

The breast cancer cell line MCF-7 (lot HTB-22) was obtained from the American Tissue Culture Collection (ATCC) and maintained in Dulbecco's H21 medium (MEM) supplemented with 10% Fetal Bovine Serum (FBS) (Hy-Clone, Logan, Utah) in a humidified atmosphere containing 5% $CO_2$ at 37° C. To establish drug resistant cell lines, MCF-7 cells were grown in the presence of either paclitaxel or doxorubicin, beginning at a concentration 1000-fold below that required to kill 50% of the cells (the $IC_{50}$). The drug concentration was increased 3-fold every two weeks (two passages), with an aliquot of the cells removed for storage in liquid nitrogen before each increase in concentration. Dose escalation continued until all cells died, after which the cells able to tolerate the highest concentration of drug were thawed for subsequent study. In this way, paclitaxel-resistant (MCF-$7_{TAX}$) and doxorubicin-resistant (MCF-$7_{DOX}$) cell lines were established. The $IC_{50}$ for each drug was determined using a clonogenic assay as outlined below. The drug resistant cells were kept in culture in the presence of the maximally tolerated drug dose. Before each experiment, the cell lines were grown for two days in the absence of drug after which fresh medium containing either calphostin C (Sigma Laboratories, Oakville, ON), doxorubicin (Adriamycin PFS®, USP, Mississauga, ON) or paclitaxel (Taxol, Bristol-Myers Squibb, Montreal, QC) was added at the concentrations indicated.

Clonogenic Assays

The sensitivity of MCF-7, MCF-$7_{TAX}$ and MCF-$7_{DOX}$ cells to calphostin C, paclitaxel or doxorubicin was determined using a clonogenic assay [33, 41]. Briefly, $2.5 \times 10^5$ cells were seeded into 25 $cm^2$ tissue culture flasks in Dulbecco's H21 medium supplemented with 10% FBS. The cells were allowed to grow overnight, after which the medium was removed and replaced with medium containing varying concentrations of paclitaxel, doxorubicin, or calphostin C (after 2 hours of light exposure to activate the molecule). After 24 hours, the medium (including any floating cells) was transferred to 14 ml screw-capped tubes and centrifuged at 1000 rpm for 10 min. The adherent cells were then released from their flasks by trypsin treatment and suspended in 10 ml of H21 medium. The cell suspension was transferred to the previous tube and all cells harvested by centrifugation. The cell pellet was washed one more time with drug-free medium and resuspended in 300 µl of normal growth medium containing FBS. The cells were then added to 2.7 ml of a methylcellulose solution. The methylcellulose medium was prepared by combining 70 ml of a 2.6% (w/v) methylcellulose solution [Shin-Etsu Chemical Co., Tokyo, Japan] in Iscove's medium (Princess Margaret Hospital, Toronto, ON) with 30 ml of FBS. Three ml syringes equipped with a 16-gauge needle were used for transferring the viscous medium. The mixture was vigorously vortexed for 10 s to ensure an even distribution of cells within the viscous medium. The vortexed samples were then allowed to sit for 30 min to remove air bubbles. A 1.2 ml aliquot of the cell suspension was then transferred to a 6-well plate and the cells allowed to grow until colonies of >50 cells were visible by light microscopy for the various cell lines in the absence of drug. The colonies present in 5 randomly selected fields were then counted by visual inspection.

Activation and Treatment of Cells with Calphostin C

Calphostin C (Sigma Laboratories, Oakville, ON) was prepared as a 100 µM stock solution in dimethylsulfoxide (Sigma Laboratories, Oakville, ON) and stored at −70° C. in 100 µl aliquots. Treatment of cells with calphostin C was based on a procedure described by Dubauskas et al. [37]. MCF-7, MCF-$7_{TAX}$ and MCF-$7_{DOX}$ cells were grown in the absence of drug for two days to 50-60% confluence, and then incubated with calphostin C at various concentrations for 24 to 48 hours. Frozen aliquots of stock calphostin C were thawed immediately prior to addition to growth medium. After addition of calphostin C to the medium, the culture plates were placed in a laminar flow tissue culture hood (Baker Company, Sanford, Me.) for two hours with covers removed at a 70 cm distance from two 80 W fluorescent light sources. The covers were then replaced, and the cells incubated in the dark under standard tissue culture conditions for the required time duration.

Fluorescence Microscopy

For microscopic observation, cells were seeded onto standard glass coverslips in 10 cm tissue culture plates with 10 ml of H21 medium and grown for 2 days until 40-50% confluence was obtained. After treatment with paclitaxel, doxorubicin or calphostin C, the cells on the glass coverslips were washed twice with PBS (2.7 mM KCl, 1.0 mM $KH_2PO_4$, 137 mM NaCl, 10 mM $Na_2HPO_4$, pH 7.4) and stained with acridine orange/ethidium bromide (each at 4 µg/ml in PBS) for 10 min at 37° C. [42]. The coverslips were then washed three times in PBS and mounted onto standard glass slides for morphological evaluation. For propidium iodide (PI) staining, the cells on coverslips were washed twice with PBS and fixed in methanol (cooled to −20° C.) for 20 min. Thirty µl of propidium iodide (PI) staining solution (100 µg/ml PI, 0.1% sodium citrate, 100 µg/ml RNase A and 0.3% Nonidet P-40) were then applied to the coverslips for 5 min. After washing 3 times with PBS, the coverslips were mounted onto glass slides. The cells were then examined using a Zeiss Axiovert 100 inverted fluorescence microscope. The filters used in the experiments were an Endow GFP Bandpass filter (exciter HQ470/40x, emitter HQ525/50m) and a Rhodamine filter (exciter D540/25x, emitter D605/55m). Both were obtained from Chroma Laboratories, Brattleboro, Vt. For each sample, the number of dead cells was determined by visualization after ethidium bromide staining, whereby only dead cells which have lost membrane integrity allow entry of cell-impermeable ethidium bromide into cells to complex with DNA and induce bright red fluorescence. Images of the cells were taken using the different filters consecutively with a 63× objective lens and an Optronics 3 CCD color camera (Carl Zeiss, Mississauga, ON). The images were recorded and overlayed using Northern Eclipse software (Empix Imaging Inc., Mississauga, ON).

Flow Cytometric Analysis

Figure 4:
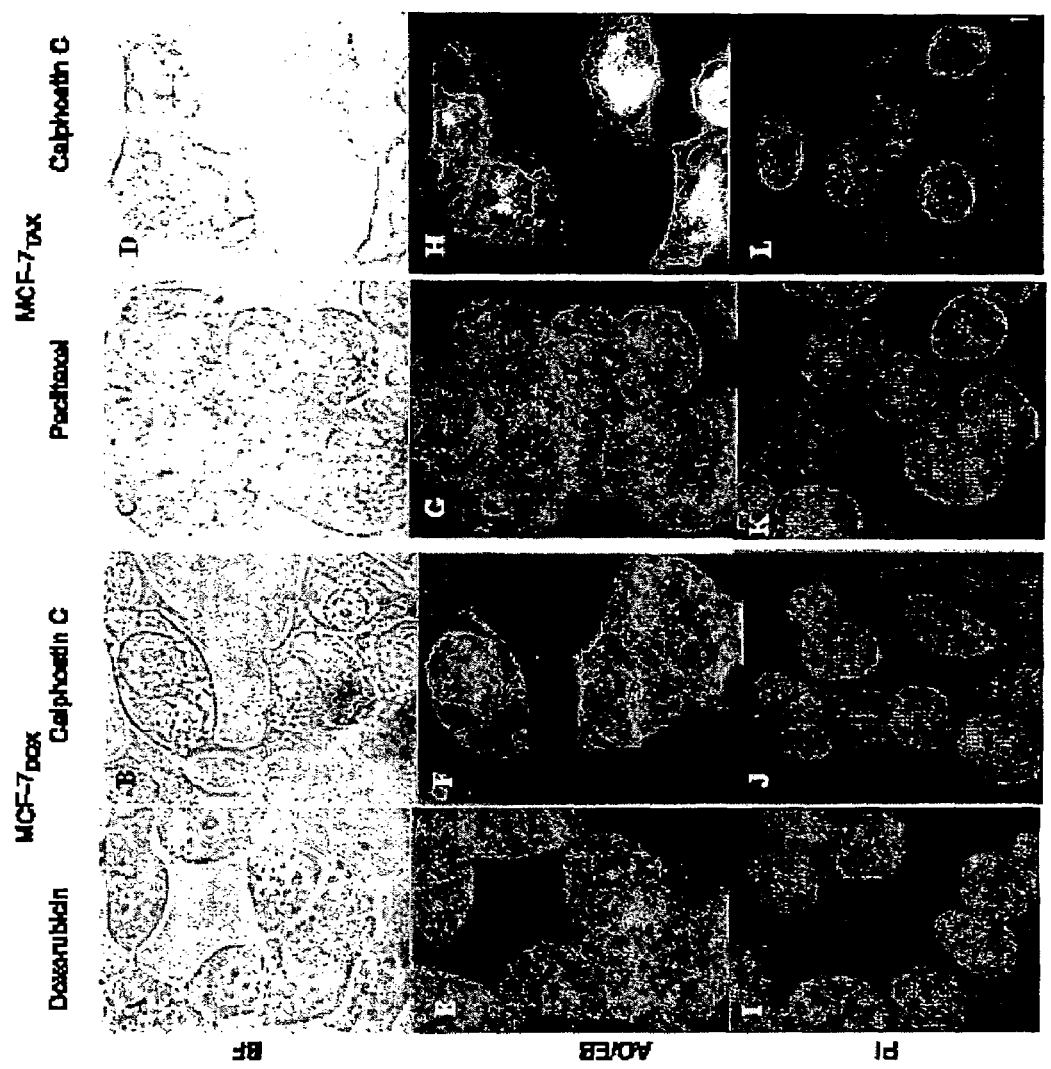
FIG. 4 illustrates the microscopic visualization of MCF-$7_{DOX}$ and MCF-$7_{TAX}$ cells after treatment with paclitaxel, doxorubicin, or calphostin C. MCF-$7_{DOX}$ cells were treated with 2 µM doxorubicin (A, E, I) or 100 nM calphostin C (B, F, J) for 24 hours. Similarly, MCF-$7_{TAX}$ cells were examined after treatment with 10 nM paclitaxel (C, G, K) or 50 nM calphostin C (D, H, L) for 24 h. Calphostin C was activated by exposure to fluorescent light for 2 h at the beginning of the experiment. Cells were visualized by bright field (BF) illumination, after staining with acridine orange/ethidium bromide (AO/EB), or after staining with propidium iodide (PI).

For flow cytometric analysis, cells at about 50% to 60% confluence were released from their flasks by trypsin treatment and washed with PBS. After centrifugation at 1000 rpm for 5 min, cells were then fixed by resuspension in 75% ethanol for 2 hours, collected by centrifugation, and resuspended in PI staining solution (see above) for 1 h. For each sample, approximately $2 \times 10^4$ cells were analyzed using a Beckman Coulter Epics® Elite flow cytometer. Fluorescence intensity upon stimulation with an argon-ion laser at 488 nm was measured using the PMT4 channel (625DL filter) and plotted against cell number. The percentage of cells with a sub-G1 DNA content was determined by the flow cytometer, adjusting the gates such that only cells with a fluorescence lower than the peak for untreated cells in G1 are counted (see FIG. 4).

Hematoxylin/Eosin Staining

For staining with hematoxylin and eosin, cells were grown in a six-well culture plate with each well containing a Snowcoat X-Tra™ microscope slide (Surgipath Laboratories, MB) immersed in 3 ml of H21 medium. When the cells reached 50% confluence, they were treated with 0-300 nM calphostin C, followed by a 2 hour exposure of the cultures to fluorescent light as described above. After light activation, the cells were placed in a 37° C. humidified incubator with 5% $CO_2$ and incubated for an additional 22 hours. The cells were then stained with hematoxylin and eosin using a previously described procedure [33, 43]. Briefly, the media was removed from cell cultures and the cells that remained adhered to the slides were washed with PBS, fixed in formalin:acetone (1:2) for 2 min, and allowed to air dry for 10 min. After washing with distilled water, 250 µl of hematoxylin solution (BDH Chemicals, Toronto, ON) was placed on each slide and allowed to incubate with the cells for 5 min. The slides were then washed with distilled water, Scott's tap water (20 g $MgSO_4.7H_2O$, 1.5 g $NaHCO_3$ in 1 L $H_2O$), and a final wash with distilled water. The cells on the slides were then stained for 5 min in 250 µl of eosin solution (100 ml of 1% eosin, 10 ml of 1% phyloxine, 4 ml of glacial acetic acid, and 780 ml of 95% ethanol). The cells were then dehydrated by washing three times in 95% ethanol and twice in 100% ethanol. The small slide was then mounted on a standard microscope glass slide, and 10 randomly selected fields were viewed at 100× magnification and photographed. For each concentration of calphostin C, the total number of dead cells in each field was ascertained and expressed relative to the total number of cells in the field. Dead cells were much smaller, exhibited dark staining and had no distinction of nucleus and cytoplasm.

Preparation of Mitochondrial and Cytoplasmic Fractions for Measurement of Cytochrome C Release For preparation of mitochondrial and cytoplasmic cellular fractions, MCF-7, MCF-$7_{TAX}$, and MCF-$7_{DOX}$ cells were grown in a monolayer to 70-90% confluence on 10 cm tissue culture plates. Twenty-four hours prior to extraction, the cells were treated with 50 nM light-activated calphostin C as described above. After this treatment, the cells were trypsinized, centrifuged at 1000 rpm in a Beckman GP centrifuge and washed with PBS. To the resulting cell pellet, 1 ml of ice-cold homogenization (HM) buffer was added. This buffer consisted of 85.55 g sucrose, 1.406 g MOPS, 0.292 g EDTA, and 1 ml ethanol per liter of solution, with a final pH of 7.2. Prior to use, 0.2 ml of 0.1 M PMSF, 1 Complete™ protease inhibitor tablet (Roche Diagnostics, Laval, QC), and 20 µl of 1 M DTT was added for 100 ml of HM buffer. Cells were then lysed 10 times by homogenization in a 2 ml dounce homogenizer. Nuclei in the lysate were then pelleted by centrifugation in a microfuge tube at 70 g for 10 minutes at 4° C. and the supernatant carefully removed. The supernatant was clarified by centrifugation at 1950 g for 10 minutes at 4° C. and the pellet (containing mitochondria) was resuspended in 50 µl of HM buffer. The remaining clarified supernatant was deemed the cytoplasmic fraction. Both mitochondrial and cytoplasmic fractions were stored at −80° C. until future use in immunoblotting experiments with cytochrome C antibodies to determine the amount of cytochrome C associated with the two fractions.

Preparation of Whole Cell Extracts for Immunoblotting Experiments

Extraction of proteins from whole cells was performed using RIPA buffer (1% NP40, 0.5% sodium deoxycholate, 0.1% SDS, 1 Complete™ protease inhibitor tablet in 50 ml of PBS). Prior to use, the RIPA buffer (50 ml) was supplemented with 500 µl each of both 100 mM sodium orthovanadate and 10 mg/ml phenylmethylsulfonyl fluoride. Cultured cells were grown as a monolayer and allowed to reach 70-90% confluence in 10 cm tissue culture plates. Twenty-four hours prior to extraction, the cells were treated with 50 nM light-activated calphostin C and incubated for another twenty-two hours under standard mammalian cell culture conditions. The culture medium was removed and the cells rinsed twice with PBS. To each flask, 0.9 ml of chilled RIPA buffer was added. The cells were scraped from the flask using a Teflon tape-coated razor blade, transferred to a 1.5 ml microfuge tube, and passed repeatedly through a 21 gauge needle to ensure efficient cell lysis and to shear any DNA present. The lysates were then incubated on ice for 30 minutes and clarified by centrifugation at 15,000 g for 20 minutes at 4° C. Samples were mixed well and several 50 µl aliquots stored in 0.5 ml microfuge tubes at −80° C.

Immunoblotting Analysis

For immunoblotting experiments using whole cell extracts, 50 µg of protein was loaded into each lane of a 10% SDS-polyacrylamide gel, on duplicate gels. After electrophoresis, the resolved proteins were then transferred to a nitrocellulose membrane, and the membranes blocked for one hour in 20 mM Tris, 100 mM NaCl, pH 7.5 (TBS), supplemented with 5% (w/v) milk powder. After blocking, the membranes were then probed with a caspase-8 rabbit polyclonal antibody (1:1000 dilution, Stressgen Biotechnologies, Victoria, BC), or a poly-ADP ribose polymerase (PARP) mouse monoclonal antibody (1:2000 dilution, BD PharMingen, Mississauga, ON), in TBS solution (supplemented with 0.1% Tween-20 (TBST) and 5% milk powder) for 1.5 hours at room temperature. The probed membranes were washed exhaustively with TBST, after which they were probed with the appropriate HRP-conjugated secondary antibody (1:10,000 dilution in TBST/5% milk powder) for 1 hour at room temperature. After the secondary antibody incubation, the membranes were washed exhaustively in TBST, incubated with ECL chemiluminescence substrates (Amersham Biosciences, Baie d'Urfé, QC) for 1 minute, sealed in plastic, and exposed to a Kodak X-OMAT film.

For measurement of cytochrome C levels associated with cytoplasmic and mitochondrial fractions of cells, the procedure described above was used, except that 20 µg of mitochondrial or cytosolic proteins were loaded into each well of the SDS-polyacrylamide gel. A mouse monoclonal cytochrome C antibody from Santa Cruz Biotechnologies (Santa Cruz, Calif.) at a 1:1000 dilution was used as the primary antibody.

EXAMPLES

Example 1

Establishment of MCF-$7_{TAX}$ and MCF-$7_{DOX}$ Cell Lines

After selection using the dose escalation protocol described above, paclitaxel- and doxorubicin-resistant cell lines (MCF-$7_{TAX}$ and MCF-$7_{DOX}$ cells, respectively) were established. The concentration of drug required to kill or inhibit the growth of 50% of MCF-7 cells (the $IC_{50}$) was 0.5 nM for paclitaxel and 10 nM for doxorubicin. In contrast, the $IC_{50}$ of MCF-$7_{TAX}$ cells for paclitaxel was 27 nM which is 54-fold higher than that for MCF-7 cells (FIG. 1A). Similarly, when MCF-7 cells acquired resistance to doxorubicin, the $IC_{50}$ of MCF-7$_{DOX}$ cells for doxorubicin increased 60-fold to 600 nM (FIG. 1B). Therefore a similar range of resistance was achieved for the two cell lines to their respective drugs.

Example 2

Calphostin C can Effectively Kill both MCF-7$_{TAX}$ and MCF-7$_{DOX}$ Cells

The ability of calphostin C to kill MCF-7$_{TAX}$ and MCF-7$_{DOX}$ cells was then examined using a clonogenic assay. As shown in FIG. 1C, calphostin C killed MCF-7$_{TAX}$ cells as effectively as parental MCF-7 cells. The $IC_{50}$'s were 13.2 nM and 9.2 nM for MCF-7 and MCF-7$_{TAX}$ cells, respectively. The induction of cell death was somewhat less effective for MCF-7$_{DOX}$ cells, which had an $IC_{50}$ for calphostin C of 64.2 nM. Thus, MCF-7$_{DOX}$ cells were approximately 5-fold less sensitive to calphostin C than MCF-7 cells. Nevertheless, the above data is strongly predictive that calphostin C may be useful for inhibiting the growth of breast tumor cells after the establishment of paclitaxel or doxorubicin resistance. This is particularly noteworthy considering the observation that MCF-7$_{DOX}$ cells are approximately 4000-fold cross-resistant to paclitaxel.

Figure 2:
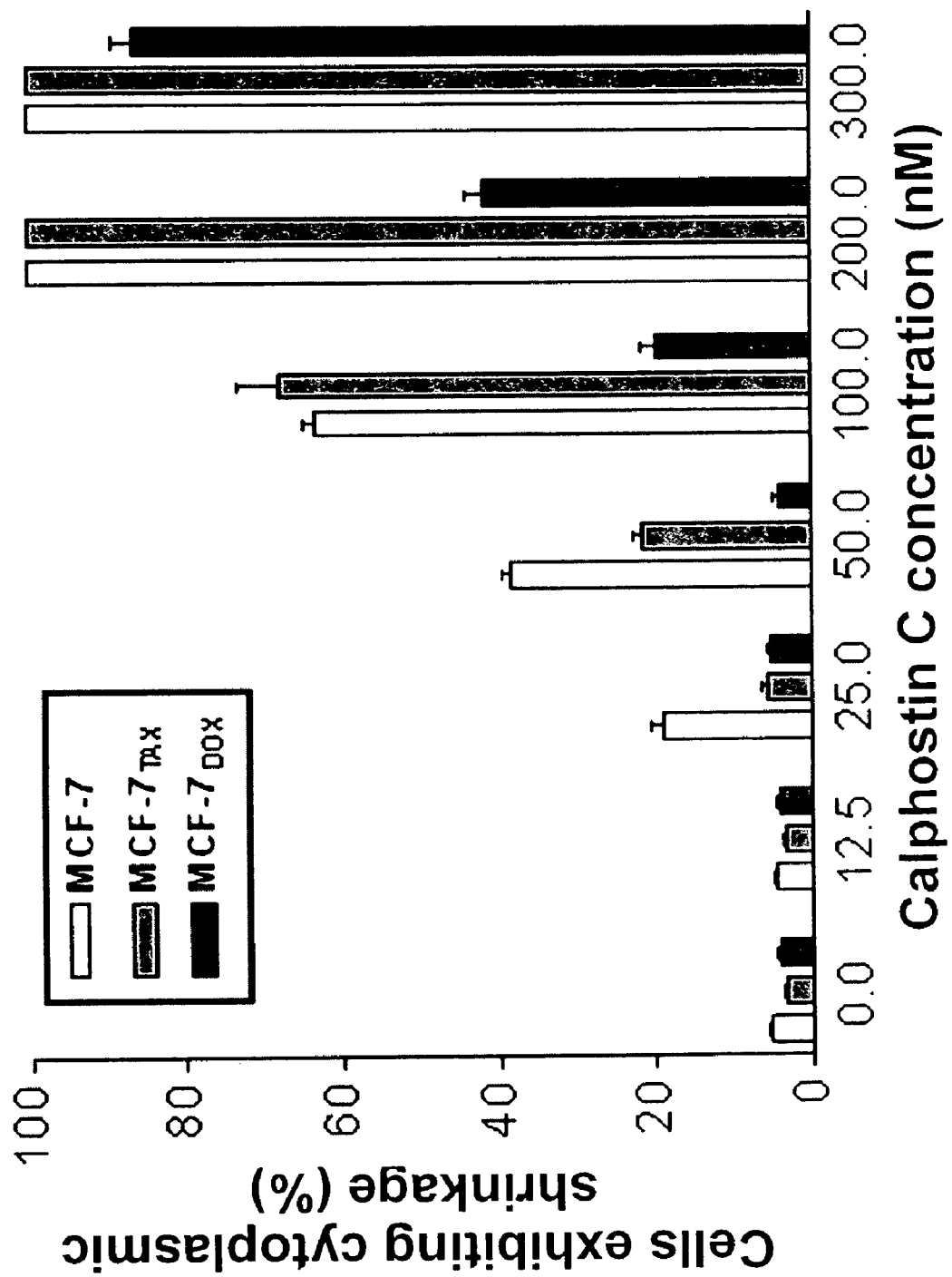
FIG. 2 illustrates the relationship between calphostin C concentration and the percentage of MCF-7, MCF-$7_{TAX}$, and MCF-$7_{DOX}$ cells exhibiting cytoplasmic shrinkage as measured by microscopic visualization after eosin/eosin staining. Each bar represents the average percentage of cells exhibiting cytoplasmic shrinkage (+/−S.E.) for 10 randomly selected fields. This figure is representative of three experiments.

The above findings were further supported by measurement of calphostin C-induced cytoplasmic shrinkage as detected using hematoxylin/eosin staining (FIG. 2). The percentage of MCF-7 cells exhibiting cytoplasmic shrinkage was initially very low (~5%), and did not increase until the concentration of calphostin C reached 25 nM. At this concentration, the percentage of MCF-7 cells exhibiting cytoplasmic shrinkage increased to 20%, while both MCF-7$_{TAX}$ and MCF-7$_{DOX}$ cells remained unchanged. With the addition of 50 nM calphostin C, the percentage of cells exhibiting cytoplasmic shrinkage increased to 35% and 23% for MCF-7 and MCF-7$_{TAX}$ cells, respectively. Cytoplasmic shrinkage was not observed in the MCF-7$_{DOX}$ cells until a calphostin C concentration of 100 nM was reached. A calphostin C concentration of 300 nM was required for all cell lines to exhibit complete cytoplasmic shrinkage. These results are consistent with the cross-resistance to calphostin C exhibited by MCF-7$_{DOX}$ cells in clonogenic assays (FIG. 1). Moreover, the observation that calphostin C induces cytoplasmic shrinkage in a dose-dependent manner, shows that the agent likely induces the death of breast tumor cells, rather than simply inhibiting their growth.

Example 3

Morphology of Paclitaxel- or Doxorubicin-Treated MCF-7 Cells

Figure 3:
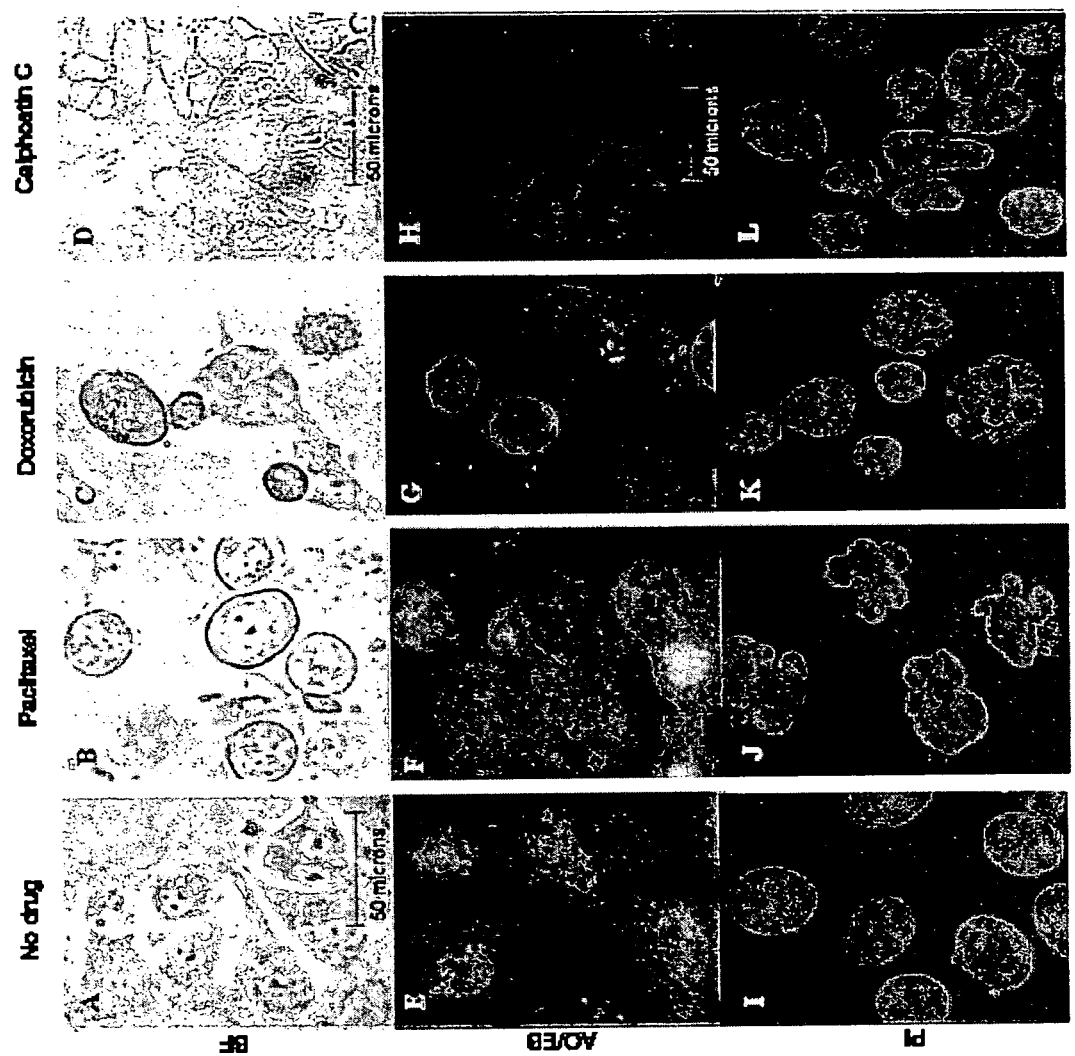
FIG. 3 illustrates the microscopic examination of control MCF-7 cells (A, E, I) and MCF-7 cells treated with 10 nM paclitaxel (B, F, J), 2 µM doxorubicin (C, G, K) or 50 nM calphostin C (D, H, L) for 24 h. The calphostin C in cultures was activated by exposure to fluorescent light for 2 h at the beginning of the experiment. Representative images of various cells were taken with bright field (BF) illumination, after staining with acridine orange/ethidium bromide (AO/EB) or after staining with propidium iodide (PI). Some MCF-7 cells treated with doxorubicin lost membrane integrity as indicated by their round very bright fluorescence associated with ethidium bromide entry.

In contrast to control cells (FIGS. 3A, 3E, and 3I), MCF-7 cells treated for 24 hours with 10 nM paclitaxel became round (hence, their unfocussed appearance) and/or detached from their culture dishes (FIGS. 3B and 3F), consistent with the action of paclitaxel as an inducer of cell cycle arrest during mitosis [44, 45]. While most of the paclitaxel-treated cells could not be stained with PI due to their detachment from coverslips during washing and staining, over 60% of adherent cells were clearly multinucleated, possessing numerous small nuclei (FIG. 3J). Multinucleation is exhibited in a number of cell lines upon treatment with paclitaxel [46, 47], including MCF-7 cells [48]. Detached paclitaxel-treated MCF-7 cells, when introduced into drug-free medium, re-adhered to the culture dish, retained their multinucleated phenotype, but could not undergo subsequent cell division (data not shown). In contrast, MCF-7 cells treated with 2 µM doxorubicin for 24 hours were often smaller in size with a very rough cell surface (FIG. 3C) and clear membrane blebbing when stained with acridine orange/ethidium bromide (FIG. 3G). Membrane blebbing has been demonstrated in a variety of cell types when treated with doxorubicin, including human melanoma and erythroleukemia cells [49], as well as human leukemia T-lymphocytes [50]. When adherent doxorubicin-treated cells were stained with PI, the nuclei appeared smaller and the intensity of staining varied throughout the nucleus (FIG. 3K). Taken together, the observed morphology of doxorubicin-treated cells is consistent with its known mode of action as a DNA-damaging agent and is clearly distinct from that of paclitaxel-treated cells (which exhibit multinucleation).

Example 4

Calphostin C Induces Cytoplasmic Vacuolization and Reduced Nuclear Staining in MCF-7, MCF-7$_{TAX}$, and MCF-7$_{DOX}$ Cells Upon incubation of MCF-7 cells with 50 nM light-activated calphostin C, MCF-7 cells showed very different cell morphology compared to that induced by paclitaxel or doxorubicin. Calphostin C caused neither membrane blebbing nor multinucleation, but induced substantial cytoplasmic vacuolization (FIGS. 3D and 3H). Over 50% of MCF-7 cells showed a number of vacuoles or "holes" of various sizes within the cytoplasm, surrounding a distinct nucleus. The vacuoles appear to lack content as evidenced by their inability to be stained with acridine orange/ethidium bromide (FIG. 3H) or hematoxylin/eosin (data not shown).

As expected, MCF-7$_{DOX}$ and MCF-7$_{TAX}$ cells treated with 2 µM doxorubicin (FIGS. 4A and 4E) or 10 nM paclitaxel (FIGS. 4C and 4G), respectively, exhibited no change in morphology over untreated cells which is consistent with their being drug resistant. Interestingly, when MCF-7$_{TAX}$ cells were treated with calphostin C, morphological changes similar to that observed in drug-sensitive MCF-7 cells were observed, including the induction of cytoplasmic vacuolization (FIGS. 4D and 4H). MCF-7$_{DOX}$ cells treated with 50 nM calphostin C also exhibited a similar phenotype (FIGS. 4B and 4F). However, the percentage of cells exhibiting cytoplasmic vacuolization was typically lower (FIGS. 4B and 4F). If the concentration of calphostin C was increased to 300 nM, the number of cells showing cytoplasmic vacuolization increased considerably to equal that obtained for MCF-7 and MCF-7$_{TAX}$ cells when treated with 50 nM calphostin C (data not shown). This is consistent with the 5-fold lower sensitivity of MCF-7$_{DOX}$ cells to calphostin C compared to MCF-7 cells in my clonogenic assays (FIG. 1C), suggesting that there is a correlation between calphostin C cytotoxicity and the induction of cytoplasmic vacuolization. Taken together, and without wishing to be restricted to any particular theory of its mode of action, the above findings suggest that the mechanism by which calphostin C kills MCF-7, MCF-7$_{DOX}$ and MCF-7$_{TAX}$ cells involves the induction of cytoplasmic vacuolization.

Example 5

Figure 5:
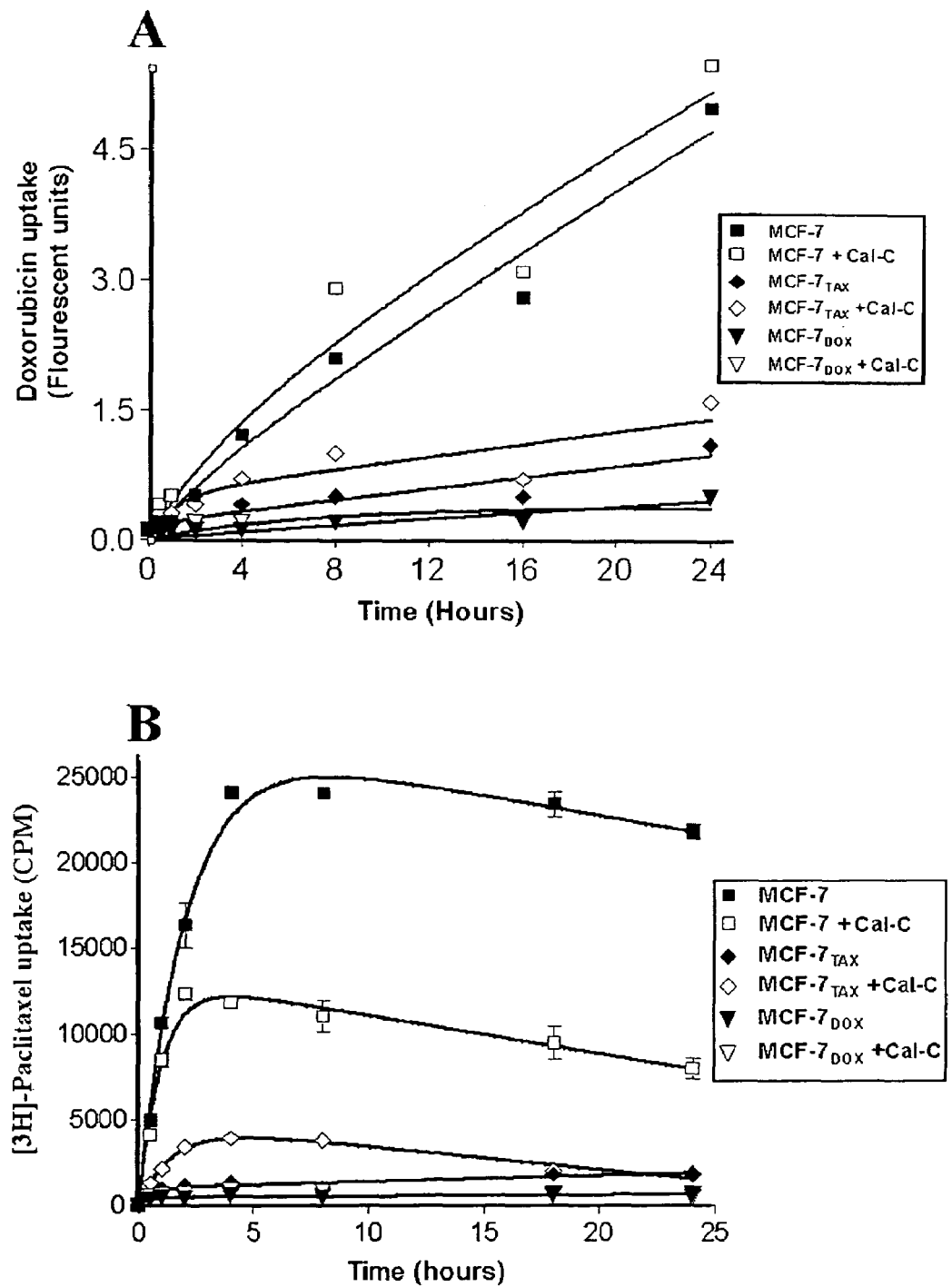
FIG. 5 illustrates the effect of calphostin C (Cal-C) on drug uptake in MCF-7 (square symbols), MCF-$7_{TAX}$ (diamond symbols) and MCF-$7_{DOX}$ (triangular symbols) cells. After one-day growth, the cells were left untreated (closed symbols) or treated with 100 nM calphostin C for 2 h with light activation (open symbols). Cells were then washed and the medium replaced with medium containing 2 µM of doxorubicin (A) or [$^3$H]-paclitaxel (B). The cells were then trypsinized and drug accumulation measured by flow cytometry (A) or liquid scintillation counting (B) at indicated time points. The figures are representative of three independent experiments.

Effects of Calphostin C on Paclitaxel or Doxorubicin Accumulation Cannot Account for its Ability to Kill MCF-7, MCF-7$_{TAX}$ or MCF-7$_{DOX}$ Cells As shown in FIG. 5, the uptake of paclitaxel and doxorubicin is dramatically lower in both MCF-7$_{DOX}$ and MCF-7$_{TAX}$ cells compared to MCF-7 cells. This shows that resistance to paclitaxel and doxorubicin in these cell lines is probably due, at least in part, to a strong reduction in drug accumulation (without wishing to be restricted to any particular theory as to a mode of action). Consistent with these findings is the observation of elevated P-gp expression in MCF-7$_{TAX}$ and MCF-7$_{DOX}$ cells compared to wildtype MCF-7 cells, which lack P-gp expression. Since calphostin C appears to directly and indirectly inhibit P-gp function [36, 39, 51] and without intending to be restricted to any particular theory of mechanism of action, it is possible that this agent may help kill drug-resistant breast tumour cells by increasing the uptake of paclitaxel or doxorubicin into drug-resistant MCF-7$_{DOX}$ and MCF-7$_{TAX}$ cells. However, the findings (FIG. 5A) suggest that calphostin C has little ability to re-establish doxorubicin uptake in either cell line. In contrast, paclitaxel uptake was slightly restored early time points for MCF-7$_{TAX}$ cells when treated with calphostin C, but drug accumulation decreased back to the levels seen in the untreated control by 18 hours (FIG. 5B). Calphostin C had little effect on paclitaxel uptake in the MCF-7$_{DOX}$ cell line. These findings suggests that calphostin C's ability to kill the drug resistant cell lines is independent of its reported effects on P-gp function and drug accumulation. Supporting this hypothesis is the observation that calphostin C can kill wildtype MCF-7 cells (which lack P-gp expression) in the absence of either paclitaxel or doxorubicin (FIG. 1). Calphostin C actually decreased paclitaxel accumulation in MCF-7 cells (FIG. 5B), possibly due to a higher combined toxicity between calphostin C and [³H]paclitaxel in these cells and a consequent decrease in drug accumulation due to cell death.

Example 6

Figure 6:
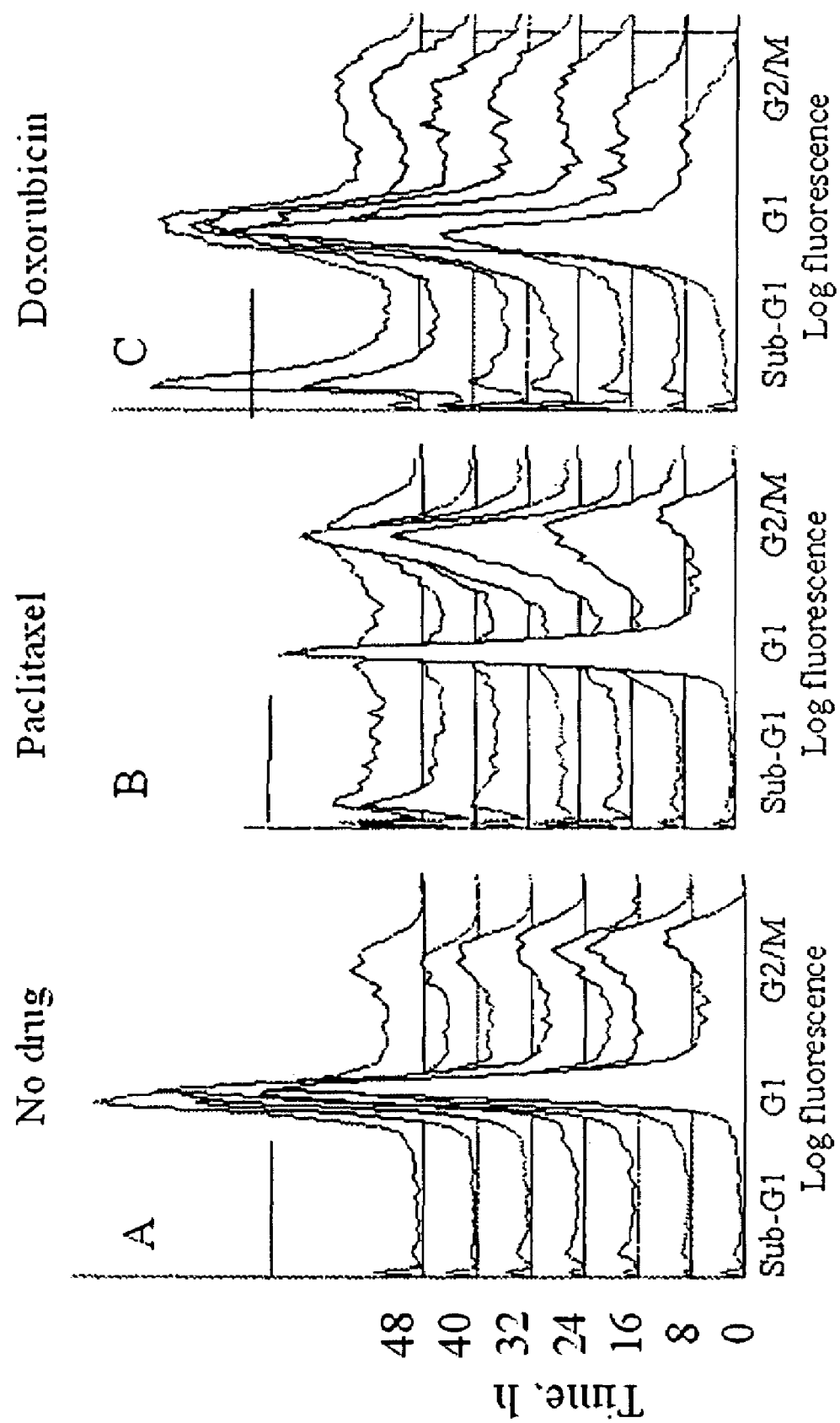
FIG. 6 shows the flow cytometric assessment of untreated MCF-7 cells (A) and MCF-7 cells treated with 10 nM paclitaxel (B) or 2 µM doxorubicin (C). Cells were removed from their flasks every 8 h, fixed with ethanol, and stained with propidium iodide. The bar indicates the fluorescence range corresponding to a sub-G1 DNA content. This figure is representative of three independent experiments.
Figure 7:
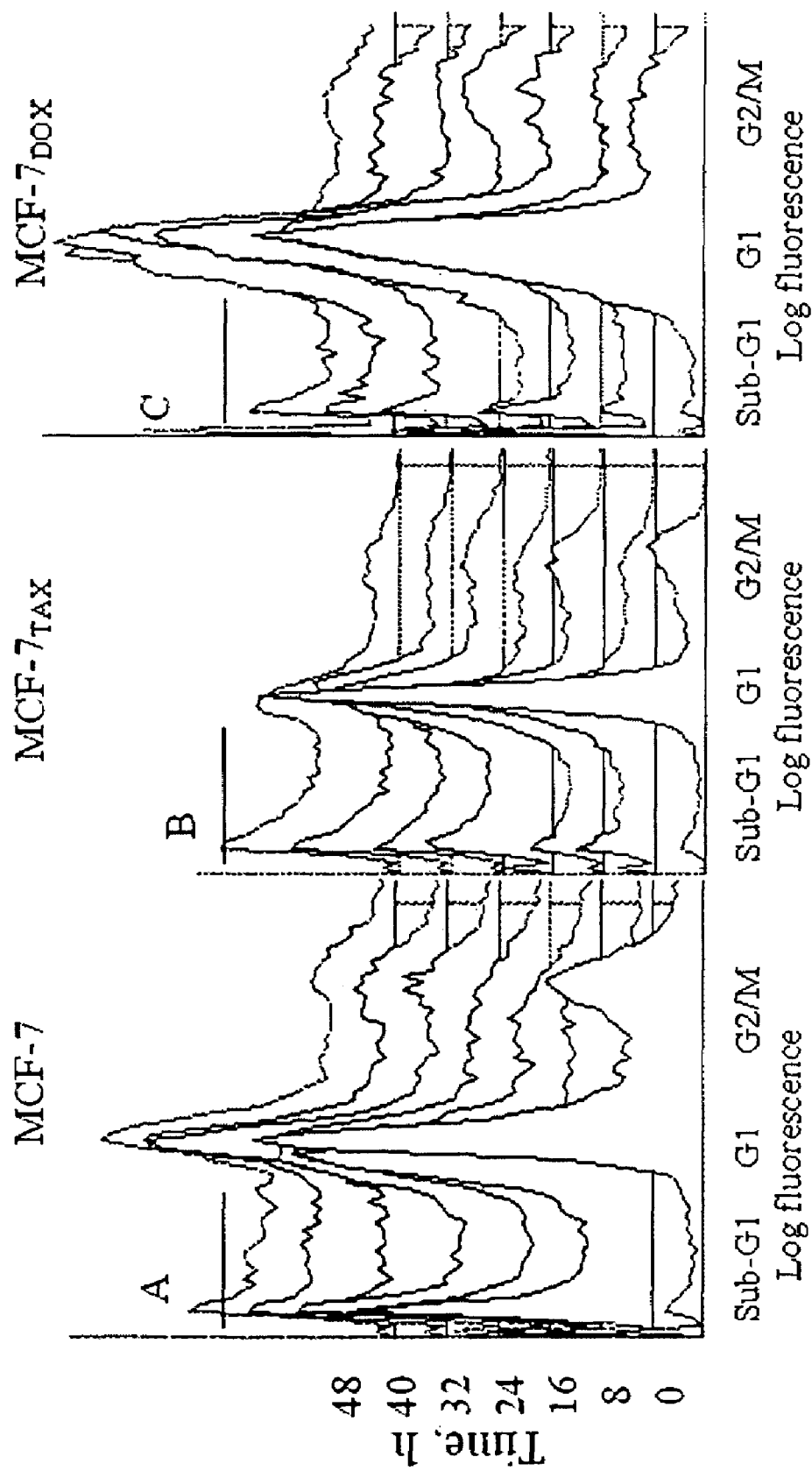
FIG. 7 is the flow cytometric assessment of MCF-7 (A), MCF-$7_{TAX}$ (B) and MCF-$7_{DOX}$ (C) cells treated with 100 nM calphostin C and a 2 h exposure to fluorescent light. Cells were removed from their flasks every 8 h, fixed with ethanol, and stained with propidium iodide. The bar indicates the fluorescence range corresponding to a sub-G1 DNA content. This figure is representative of three independent experiments.

Changes in Cellular DNA Content Induced by Paclitaxel, Doxorubicin and Calphostin C in Breast Tumor Cells To assess whether cellular DNA content is altered by paclitaxel, doxorubicin or calphostin C treatment, MCF-7 cells were incubated with 10 nM paclitaxel, 2 µM doxorubicin or 100 nM calphostin C, fixed, stained with propidium iodide, and analyzed by flow cytometry as described in the "Materials and Methods" section. As shown in FIG. 6B, paclitaxel treatment of MCF-7 cells induced an initial arrest in G2/M, followed by the generation of cells with a broad range of sub-G1 DNA content. This is consistent with the known mechanism of action for paclitaxel, which involves an arrest of the cell cycle in mitosis, followed by the induction of cell multinucleation and cell lysis. In contrast, MCF-7 cells treated with doxorubicin did not initially arrest in G2/M; rather, the drug induced a time-dependent increase in the number of cells with a very defined sub-G1 DNA content (FIG. 6C). Treatment of MCF-7, MCF-7$_{TAX}$ and MCF-7$_{DOX}$ cells with 100 nM light-activated calphostin C resulted in a unique cellular response, characterized by no initial accumulation in G2/M and the generation of cells with a very broad range of sub-G1 DNA content (compare FIGS. 6 and 7). Taken together, the above results further support the hypothesis that calphostin C kills breast tumor cells by a mechanism distinct from that of either paclitaxel or doxorubicin.

Figure 8:
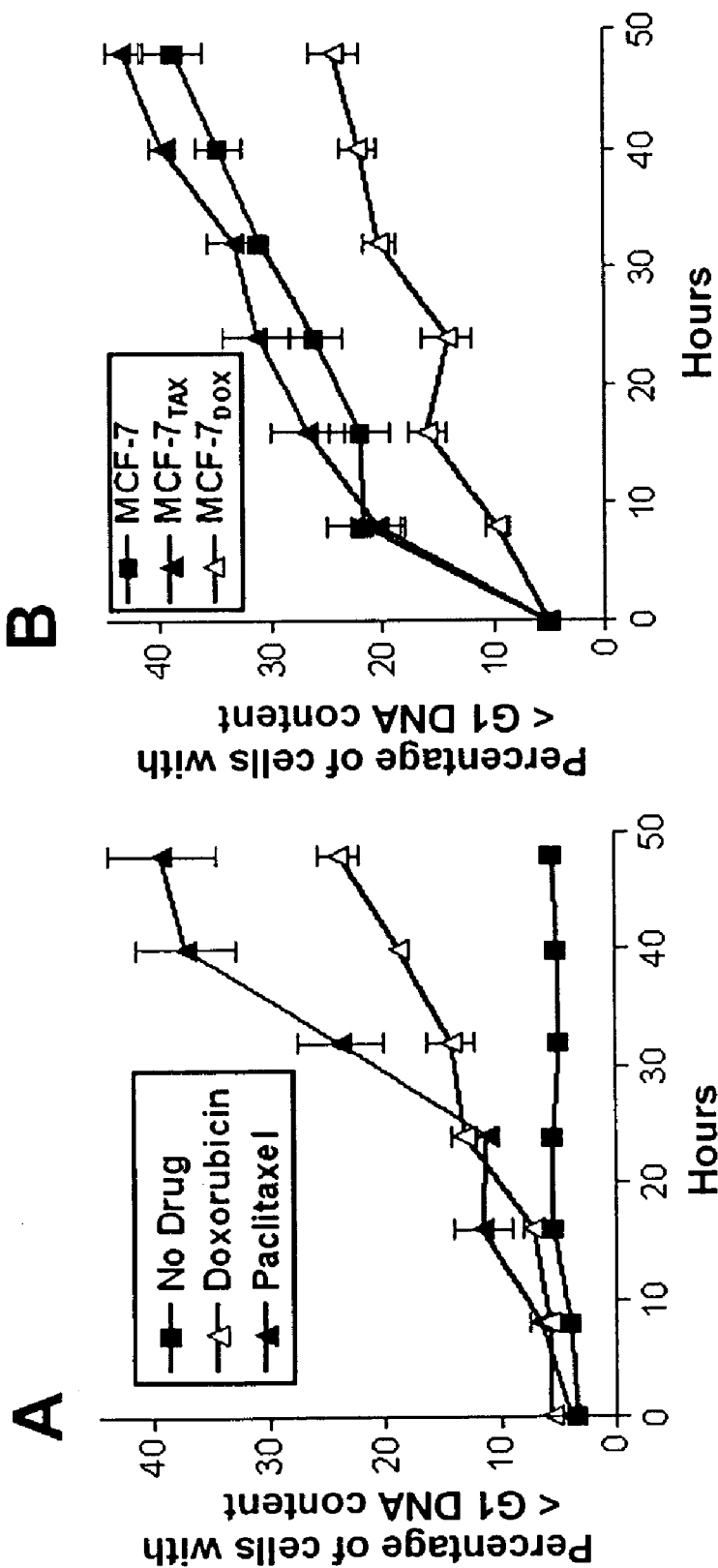
FIG. 8 illustrates—(A) Changes in the number of cells with a sub-G1 DNA content over time in response to no treatment (|), 10 nM paclitaxel (?) or 2 µM doxorubicin (?). In a second experiment (B), MCF-7 (|), MCF-7 TAX (?), and MCF-$7_{DOX}$ (?) cells were treated with 100 nM calphostin C and 2 h exposure to fluorescent light. The percentage of cells having a fluorescence corresponding to a sub-G1 DNA content was then plotted over time. The numbers represent the mean (+S.D.) for three independent experiments.

When the percentage of cells with a sub-G1 DNA content, was quantified over time (FIG. 8), it was found that paclitaxel and doxorubicin C induced a large increase in the number of cells with a sub-G1 DNA content approximately 24 hours after drug administration (FIG. 8A). In contrast, strong increases in the percentage of sub-G1 cells were observed for MCF-7, MCF-7$_{TAX}$, and MCF-7$_{ADR}$ cells as early as 8 hours after calphostin C treatment (FIG. 8B). These findings also suggest that calphostin C has a mechanism of action which is distinct from that of paclitaxel or doxorubicin. It should also be noted that MCF-7$_{DOX}$ cells treated with 100 nM calphostin C exhibited a significantly lower percentage of cells with a sub-G1 DNA content than similarly treated MCF-7 or MCF-7$_{TAX}$ cells (FIG. 8B). These results are consistent with the clonogenic assays (FIG. 1) and hematoxylin/eosin staining experiments (FIG. 2), showing a 5-fold reduction in calphostin C sensitivity compared to MCF-7 and MCF-7$_{TAX}$ cells.

Example 7

Figure 9:
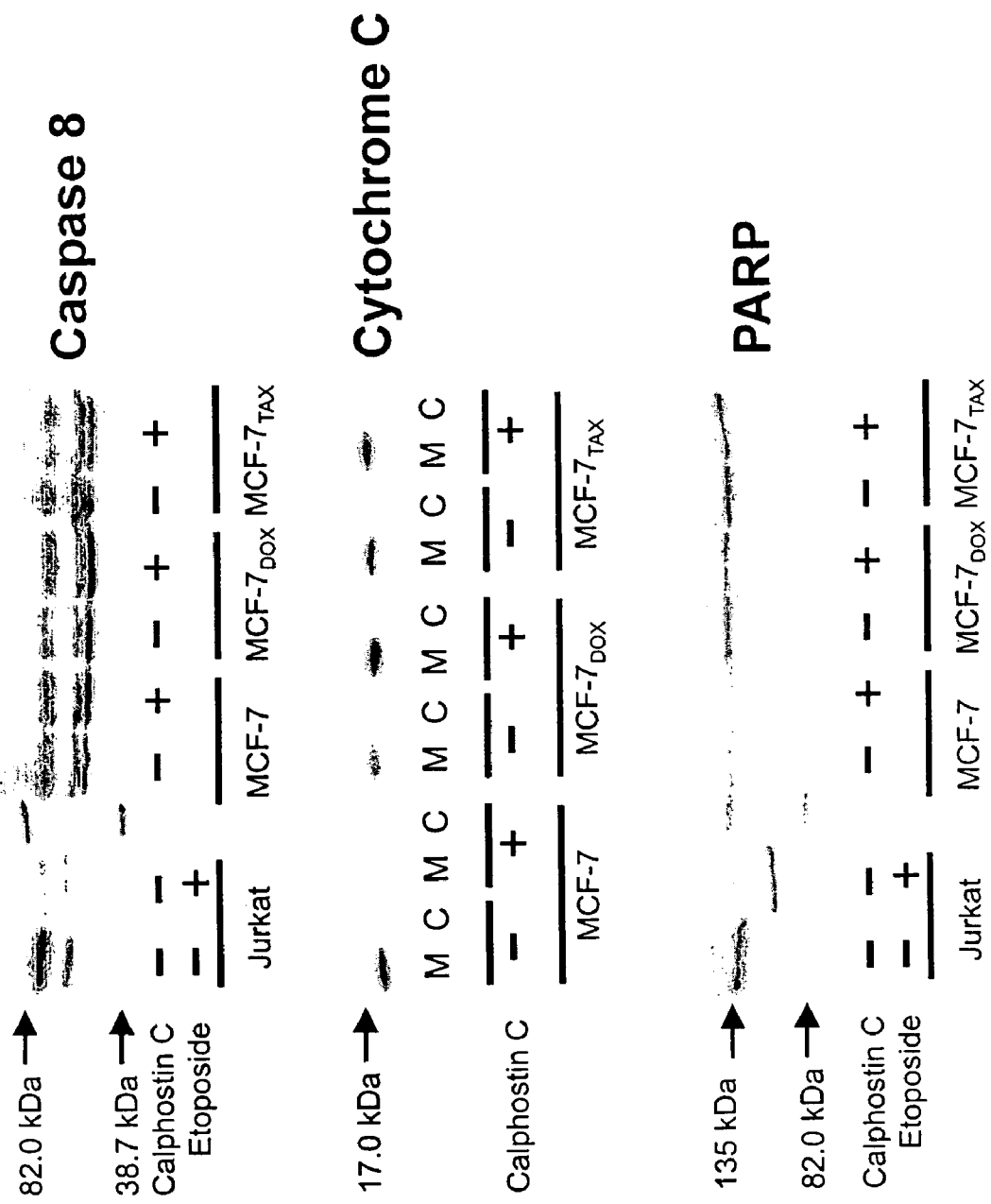
FIG. 9 illustrates the effect of calphostin C on caspase 8 cleavage, PARP cleavage, and cytochrome C release in MCF-7, MCF-7F$_{DOX}$, and MCF-$7_{TAX}$ cells. The MCF-7, MCF-7F$_{DOX}$, and MCF-$7_{TAX}$ cell lines were incubated with (+) or without (−) 100 nM calphostin C, after which whole cell extracts were monitored for caspase-8 and cytochrome C levels by immunoblotting as described in Materials and Methods. A similar experiment was also performed, except that mitochondrial (M) and cytosolic (C) fractions were prepared as described in Materials and Methods to monitor by immunoblotting the release of cytochrome C from mitochondria into the cytosol in response to calphostin C. As positive controls, similar experiments were conducted using Jurkat cells, with (+) or without (−) the addition of 3 µg/ml etoposide for 24 hours. Jurkat cells are known to exhibit caspase-8 and PARP cleavage when treated with etoposide.

Calphostin C Kills Drug-Sensitive and Drug-Resistant Tumor Cells by a Mechanism not Involving the Activation of Classic Apoptotic Pathways The generation of cells exhibiting cytoplasmic shrinkage by calphostin C suggests that the molecule may induce the killing of breast tumor cells by activating important pathways involved in the regulation of apoptosis in cells. However, calphostin C-treated cells, when visualized microscopically after acridine orange/ethidium bromide staining (FIGS. 3 and 4), did not exhibit the classic features of apoptosis (membrane blebbing, cytoplasmic shrinkage, and nuclear fragmentation) [52, 53]. To assess whether calphostin C kills breast tumors through an apoptotic mechanism, a series of early, middle, and late biochemical events known to occur in cells were monitored as they underwent apoptosis. These include the induction of caspase-8 cleavage, the release of cytochrome C from mitochondria, and the stimulation of PARP cleavage. While it was observed that, as expected [54, 55], etoposide could induce caspase-8 and PARP cleavage (degradation) in Jurkat cells (FIG. 9), treatment of MCF-7, MCF-7$_{TAX}$ and MCF-7$_{DOX}$ cells with calphostin C did not result in any change in the levels of these proteins (FIG. 9). Similarly, while the levels of cytochrome C in mitochondrial and cytoplasmic cellular fractions did vary in our experiments, there was no clear evidence for the release of cytochrome C from mitochondria in response to calphostin C treatment (FIG. 9). Taken together, these findings suggest that calphostin C kills drug-sensitive and drug-resistant breast tumor cells by a mechanism not involving the activation of classic pathways involved in apoptosis.

This invention provides for the ability of calphostin C to kill breast tumor cells highly resistant to either paclitaxel or doxorubicin. Calphostin C is effective in killing paclitaxel- and doxorubicin-resistant breast tumor cell lines and its cytotoxicity appears to be independent of its reported effects on P-gp function [36, 39, 40]. Moreover, calphostin C kills drug-resistant breast tumor cells through a mechanism distinct from the actions of either paclitaxel or doxorubicin, likely involving cytoplasmic vacuolization without the apparent induction of apoptosis.

It has been well documented that paclitaxel potently inhibits the proliferation of cancer cells by a mechanism involving the stabilization of mitotic spindle microtubules. This results in an arrest of the cells in mitosis, followed by cell multinucleation and apoptosis [45, 56, 57]. In contrast to paclitaxel, doxorubicin intercalates between DNA strands, inhibits both DNA synthesis and RNA polymerase activity [58], and enhances chromatin condensation and cell surface blebbing [49]. These findings are consistent with these contrasting mechanisms of drug action and suggest that selection for resistance to paclitaxel or doxorubicin in MCF-7 breast cancer cells blocks these mechanisms. Moreover, calphostin C, a specific inhibitor of phorbol-responsive PKC isoenzymes [35], seems to be able to kill drug-resistant breast tumor cells by a mechanism unrelated to its reported ability to modulate P-glycoprotein function. There is a strong correlation between calphostin C cytotoxicity and the induction of cytoplasmic vacuolization in both the drug-sensitive and drug-resistant cell lines. Since it is unlikely that cells would be able to survive such extensive cytoplasmic vacuolization, this may likely be the mechanism by which calphostin C kills MCF-7 breast tumor cells, although we do not intend to be restricted to any particular theory of mode of action.

Calphostin C has been tested for cytotoxicity in a wide variety of cell lines, including human bladder, human prostate and rodent prostate cancer cells [38], as well as human glioma [59], human lymphoblastic leukemia [60] and human promyelocytic leukemia [61] cells. The cytotoxic effects of calphostin C are very similar in all these cell lines and appears to be through an apoptotic mechanism involving Bax integration into mitochondria, cytochrome C release, caspase-3 activation, PARP cleavage, SAPK/JNK/p38 kinase activation, and a possible downregulation of bcl-2 transcription or translation [38, 59, 62]. Calphostin C can also play a role in the promotion of necrotic cell death by deoxycholic acid [63] and appears to be able to kill tumor cells with widely varying genetic backgrounds [37]. Apart from cytoplasmic vacuolization, calphostin C-treated MCF-7 cells also exhibited a sub-G1 DNA content, cytoplasmic shrinkage, and a localized reduction in nuclear staining, all phenotypes associated with the induction of apoptosis. To help resolve this discrepancy, we monitored the ability of calphostin C to modulate key processes involved in early, middle, and late apoptosis (caspase-8 activation, cytochrome C release from mitochondria, and cleavage of PARP, respectively). Calphostin C was unable to affect any of these processes (FIG. 9), strongly suggesting that calphostin C can also induce death without activation of classic pathways involved in the regulation of apoptosis.

It should be noted that MCF-7 cells possess a 47-base pair deletion mutation within exon 3 of caspase-3, which also appears to be associated with acquired resistance to chemotherapeutic drugs [64, 65]. While caspase-3 appears to be essential for tumor necrosis factor's ability to induce DNA fragmentation and typical morphological features associated with apoptosis in MCF-7 cells [65], it is unlikely that this mutation abrogated calphostin C's ability to stimulate cytochrome C release and PARP cleavage in MCF-7 cells, since these events are known to precede caspase-3-activation and since tumor necrosis factor can induce apoptosis and PARP cleavage in caspase-3-deficient MCF-7 cells [66]. Consequently, it would appear that calphostin C kills drug-resistant breast tumor cells by a caspase-3-independent, non-apoptotic mechanism.

It was observed that calphostin C can induce both death and cytoplasmic vacuolization in a variety of additional cell lines, including MDA-MB231 human breast cancer, MES-SA human uterine sarcoma, human 293T embryonic kidney, mouse B16BL6 melanoma and Chinese hamster ovary (CHO) cells (data not shown). These observations strongly suggest that cytoplasmic vacuolization is a general consequence of cellular exposure to activated calphostin C and that this phenomenon may be coupled to its cytotoxicity. In addition, since I observed that calphostin C kills tumor cells through an apparent non-apoptotic mechanism, a variety of tumor types with defects in key apoptotic regulatory pathways (for example, mutations in p53) may be susceptible to killing by this agent.

The invention relates to the use of calphostin C to effectively kill a variety of tumor cell types in vitro, including breast cancer cells which are highly resistant to killing by paclitaxel or doxorubicin. Without wishing to be restricted to any one theory, it is believed that calphostin C may work via a P-glycoprotein-independent, non-apoptotic mechanism accompanied by cytoplasmic vacuolization. Given its ability to kill a variety of tumor cells with widely varying genetic backgrounds and given its light-dependent cytotoxicity, calphostin C should be useful for the clinical treatment of a variety of cancers using photodynamic therapy (PDT).

A clinical PDT treatment using calphostin C may entail administration of the compound in an amount sufficient to treat a tumor which is resistant to treatment by one and preferably both of taxane and anthracycline chemotherapeutic drugs, in particular paclitaxel and doxyrubicin respectively. Such administration may be systemic or a localized administration. This is then followed by activation in the appropriate wave lengths for activation of the agent, by light, for a defined period, preferably applied only to the region of the tumor, for example by laser. Since calphostin C is relatively activated upon photo activation, the patient should be kept in a darkened environment during the treatment, apart from the localized application of light. The dosage form and amount, route of administration, length of treatment and number of times the treatment is administered is determined on the basis of therapeutic efficacy and patient safety.

Recently, its usage has been proposed for the treatment of malignant gliomas [67, 70] and bladder cancer [38] using PDT. Calphostin C has been administered successfully to rats, where it has been shown to help prevent cytokine- or PMA-induced angiogenesis [68]. Pharmacokinetic studies after treatment of mice with calphostin C (40 mg/kg) revealed a rapid drug absorption rate ($t_{1/2}$=24.2 min) and clearance rate ($t_{1/2}$=91.3 min), and that plasma concentrations of 2.9 µM could be reached in mice without significant cytotoxicity [69]. These levels are sufficient to kill tumor cells upon light activation.

The finding that calphostin C can kill paclitaxel-resistant and doxorubicin-resistant breast tumor cells results in the prediction that the drug can be used in conjunction with PDT to kill tumors in breast cancer patients which have become refractory to treatment by chemotherapy.

Thus it is apparent that there has been provided the use of calphostin C to treat human subjects for cancer which is resistant to treatment by other forms of chemotherapeutic drugs. Such cancer can be breast cancer or uterine cancer; and the other forms of chemotherapeutic drugs include taxane and anthracycline drugs, in particular, paclitaxel and doxorubicin.

Cancer treated by calphostin C in accordance with this invention can be characterized generally by tumor cells that have a defect in an apoptotic regulatory pathway which renders the cells resistant to at least some other forms of chemotherapeutic treatment.

REFERENCES:

1. Liu Z L, Onda K, Tanaka S, Toma T, Hirano T, Oka K: Induction of multidrug resistance in MOLT-4 cells by anticancer agents is closely related to increased expression of functional P-glycoprotein and MDR1 mRNA. Cancer Chemother Pharmacol 49: 391-397, 2002.
2. Gottesman M M, Fojo T, Bates S E: Multidrug resistance in cancer: role of ATP-dependent transporters. Nat Rev Cancer 2: 48-58, 2002.
3. Childs S, Ling V: The MDR superfamily of genes and its biological implications. Important Adv Oncol 21-36, 1994.
4. Cole S P, Bhardwaj G, Gerlach J H, Mackie J E, Grant C E, Almquist K C, Stewart A J, Kurz E U, Duncan A M, Deeley R G: Overexpression of a transporter gene in a multidrug-resistant human lung cancer cell line. Science 258: 1650-1654, 1992.
5. Scheffer G L, Wijngaard P L, Flens M J, Izquierdo M A, Slovak M L, Pinedo H M, Meijer C J, Clevers H C, Scheper R J: The drug resistance-related protein LRP is the human major vault protein. Nat Med 1: 578-582,1995.
6. Germann U A. P-glycoprotein—a mediator of multidrug resistance in tumor cells. Eur J Cancer 32A: 927-944, 1996.
7. Ross D D, Yang W, Abruzzo L V, Dalton W S, Schneider E, Lage H, Dietel M, Greenberger L, Cole S P, Doyle L A: Atypical multidrug resistance: breast cancer resistance protein messenger RNA expression in mitoxantrone-selected cell lines. J Natl Cancer Inst 91: 429-433, 1999.
8. Tan B, Piwnica-Worms D, Ratner L: Multidrug resistance transporters and modulation. Curr Opin Oncol 12: 450-458, 2000.
9. Kerb R, Hoffmeyer S, Brinkmann U: ABC drug transporters: hereditary polymorphisms and pharmacological impact in MDR1, MRP1 and MRP2. Pharmacogenomics 2: 51-64, 2001.
10. Fojo A, Akiyama S, Gottesman M M, Pastan I: Reduced drug accumulation in multiply drug-resistant human KB carcinoma cell lines. Cancer Res 45: 3002-3007, 1985.
11. Ambudkar S V, Dey S, Hrycyna C A, Ramachandra M, Pastan I, Goftesman M M: Biochemical, cellular, and pharmacological aspects of the multidrug transporter. Annu Rev Pharmacol Toxicol 39: 361-398, 1999.
12. Shabbits J, Krishna R, Mayer L: Molecular and pharmacological strategies to overcome multidrug resistance. Expert Rev Anticancer Ther 1: 585-594, 2001.
13. Tsuruo T, Naito M, Tomida A, Fujita N, Mashima T, Sakamoto H, Haga N: Molecular targeting therapy of cancer: drug resistance apoptosis and survival signal. Cancer Sci 94: 15-21, 2003.
14. Harris A L, Hochhauser D: Mechanisms of multidrug resistance in cancer treatment. Acta Oncol 31: 205-213, 1992.
15. Fry A M, Chresta C M, Davies S M, Walker M C, Harris A L, Hartley J A, Masters J R, Hickson I D: Relationship between topoisomerase II level and chemosensitivity in human tumor cell lines. Cancer Res 51: 6592-6595, 1991.
16. Giaccone G, Gazdar A F, Beck H, Zunino F, Capranico G: Multidrug sensitivity phenotype of human lung cancer cells associated with topoisomerase II expression. Cancer Res 52: 1666-1674, 1992.
17. Elliott T, Sethi T: Integrins and extracellular matrix: a novel mechanism of multidrug resistance. Expert Rev Anticancer Ther 2: 449-459, 2002.
18. Friesen C, Fulda S, Debatin K M: Deficient activation of the CD95 (APO-1/Fas) system in drug-resistant cells. Leukemia 11: 1833-1841, 1997.
19. Cheng A, Chuang S, Fine R, Yeh K, Liao C, Lay J, Chen D: Inhibition of the membrane translocation and activation of protein kinase C, and potentiation of doxorubicin-induced apoptosis of hepatocellular carcinoma cells by tamoxifen. Biochem Pharmacol 55: 523-531, 1998.
20. Clark A, West K, Blumberg P, Dennis P: Altered protein kinase C (PKC) isoforms in non-small cell lung cancer cells: PKCdelta promotes cellular survival and chemotherapeutic resistance. Cancer Res 63: 780-786, 2003.
21. Avendano C, Menendez J C: Inhibitors of multidrug resistance to antitumor agents (MDR). Curr Med Chem 9: 159-193, 2002.
22. Fukuda T, Kamishima T, Kakihara T, Ohnishi Y, Suzuki T: Characterization of newly established human myeloid leukemia cell line (KF-19) and its drug resistant sublines. Leuk Res 20: 931-939, 1996.
23. Boesch D, Muller K, Pourtier-Manzanedo A, Loor F: Restoration of daunomycin retention in multidrug-resistant P388 cells by submicromolar concentrations of SDZ PSC 833, a nonimmunosuppressive cyclosporin derivative. Exp Cell Res 196: 26-32, 1991.
24. Boesch D, Gaveriaux C, Jachez B, Pourtier-Manzanedo A, Bollinger P, Loor F: In vivo circumvention of P-glycoprotein-mediated multidrug resistance of tumor cells with SDZ PSC 833. Cancer Res 51: 4226-4233, 1991.
25. Efferth T, Fabry U, Osieka R: Apoptosis and resistance to daunorubicin in human leukemic cells. Leukemia 11: 1180-1186, 1997.
26. Sikic B I. Modulation of multidrug resistance: a paradigm for translational clinical research. Oncology (Huntingt) 13: 183-187, 1999.
27. Ogretmen B, Safa A R: Down-regulation of apoptosis-related bcl-2 but not bcl-xL or bax proteins in multidrug-resistant MCF-7/Adr human breast cancer cells. Int J Cancer 67: 608-614, 1996.
28. Roninson I B. *Molecular and Cellular Biology of Multidrug Resistance in Tumor Cells*. New York, Plenum Press, 1991.
29. Sikic B I. Modulation of multidrug resistance: at the threshold. J Clin Oncol 11: 1629-1635, 1993.
30. Fisher G A, Sikic B I: Clinical studies with modulators of multidrug resistance. Hematol Oncol Clin North Am 9: 363-382, 1995.
31. Fu J, Chen Z, Cen J, Ruan C: Expression of the human multidrug resistance gene mdr1 in leukemic cells and its application in studying P-glycoprotein antagonists. Chin Med J (Engl) 113: 228-231, 2000.
32. Takara K, Sakaeda T, Yagami T, Kobayashi H, Ohmoto N, Horinouchi M, Nishiguchi K, Okumura K: Cytotoxic effects of 27 anticancer drugs in HeLa and MDR1-overexpressing derivative cell lines. Biol Pharm Bull 25: 771-778, 2002.
33. Chadderton A, Villeneuve D J, Gluck S, Kirwan-rhude A F, Gannon B R, Blais D E, Parissenti A M: Role of specific apoptotic pathways in the restoration of paclitaxel- induced apoptosis by valspodar in doxorubicin-resistant MCF-7 breast cancer cells. Breast Cancer Res Treat 59: 231-244, 2000.
34. Crown J. Nonanthracycline containing docetaxel-based combinations in metastatic breast cancer. Oncologist 6 Suppl 3: 17-21, 2001.
35. Kobayashi E, Ando K, Nakano H, Iida T, Ohno H, Morimoto M, Tamaoki T: Calphostins (UCN-1028), novel and specific inhibitors of protein kinase C. I. Fermentation, isolation, physico-chemical properties and biological activities. J Antibiot (Tokyo) 42: 1470-1474, 1989.
36. Gupta S, Patel K, Singh H, Gollapudi S: Effect of Calphostin C (PKC inhibitor) on daunorubicin resistance in P388/ADR and HL60/AR cells: reversal of drug resistance possibly via P-glycoprotein. Cancer Lett 76: 139-145, 1994.
37. Dubauskas Z, Beck T P, Chmura S J, Kovar D A, Kadkhodaian M M, Shrivastav M, Chung T, Stadler W M, Rinker-Schaeffer C W: Activated calphostin C cytotoxicity is independent of p53 status and in vivo metastatic potential. Clin Cancer Res 4: 2391-2398, 1998.
38. Beck T P, Kirsh E J, Chmura S J, Kovar D A, Chung T, Rinker-Schaeffer C W, Stadler W M: In vitro evaluation of calphostin C as a novel agent for photodynamic therapy of bladder cancer. Urology 54: 573-577, 1999.
39. Bates S E, Lee J S, Dickstein B, Spolyar M, Fojo A T: Differential modulation of P-glycoprotein transport by protein kinase inhibition. Biochemistry 32: 9156-9164, 1993.
40. Matsumoto T, Tani E, Yamaura I, Miyaji K, Kaba K: Effects of protein kinase C modulators on multidrug resistance in human glioma cells. Neurosurgery 36: 565-571, 1995.
41. Keating A and Toor P. Human long term bone marrow culture. In Poclard J M, ed). New York, Wiley-Liss, 1990, pp 331.
42. Martin D and Lenardo M. Morphological, Biochemical, and Flow cytometric analysis of apoptosis. In Anonymous New York, John Wiley & Sons, Inc., 2000, pp 1-5.
43. Saunders D E, Lawrence W D, Christensen C, Wappler N L, Ruan H, Deppe G: Paclitaxel-induced apoptosis in MCF-7 breast-cancer cells. Int J Cancer 70: 214-220, 1997.
44. Horwitz S B. Mechanism of action of taxol. Trends Pharmacol Sci 13: 134-136, 1992.
45. Jordan M A, Wendell K, Gardiner S, Derry W B, Copp H, Wilson L: Mitotic block induced in HeLa cells by low concentrations of paclitaxel (Taxol) results in abnormal mitotic exit and apoptotic cell death. Cancer Res 56: 816-825, 1996.
46. Weitzel D H, Vandre D D: Differential spindle assembly checkpoint response in human lung adenocarcinoma cells. Cell Tissue Res 300: 57-65, 2000.
47. Makarovskiy A N, Siryaporn E, Hixson D C, Akerley W: Survival of docetaxel-resistant prostate cancer cells in vitro depends on phenotype alterations and continuity of drug exposure. Cell Mol Life Sci 59: 1198-1211, 2002.
48. Blajeski A L, Kottke T J, Kaufmann S H: A multistep model for paclitaxel-induced apoptosis in human breast cancer cell lines. Exp Cell Res 270: 277-288, 2001.
49. Serafino A, Sinibaldi-Vallebona P, Pierimarchi P, Bernard P, Gaudiano G, Massa C, Rasi G, Ranagnan G: Induction of apoptosis in neoplastic cells by anthracycline antitumor drugs: nuclear and cytoplasmic triggering? Anticancer Res 19: 1909-1918, 1999.
50. da Silva C P, de Oliveira C R, da Conceicao M, de Lima P: Apoptosis as a mechanism of cell death induced by different chemotherapeutic drugs in human leukemic T-lymphocytes. Biochem Pharmacol 51: 1331-1340, 1996.
51. Conseil G, Perez-Victoria J M, Jault J M, Gamarro F, Goffeau A, Hofmann J, Di Pietro A: Protein kinase C effectors bind to multidrug ABC transporters and inhibit their activity. Biochemistry 40: 2564-2571, 2001.
52. Robertson A M, Bird C C, Waddell A W, Currie A R: Morphological aspects of glucocorticoid-induced cell death in human lymphoblastoid cells. J Pathol 126: 181-187, 1978.
53. Sheridan J W, Bishop C J, Simmons R J: Biophysical and morphological correlates of kinetic change and death in a starved human melanoma cell line. J Cell Sci 49: 119-137, 1981.
54. Sun X M, MacFarlane M, Zhuang J, Wolf B B, Green D R, Cohen G M: Distinct caspase cascades are initiated in receptor-mediated and chemical-induced apoptosis. J Biol Chem 274: 5053-5060, 1999.
55. Wesselborg S, Engels I H, Rossmann E, Los M, Schulze-Osthoff K: Anticancer drugs induce caspase-8/FLICE activation and apoptosis in the absence of CD95 receptor/ligand interaction. Blood 93: 3053-3063, 1999.
56. Jordan M A, Toso R J, Thrower D, Wilson L: Mechanism of mitotic block and inhibition of cell proliferation by taxol at low concentrations. Proc Natl Acad Sci USA 9552-9556, 1993.
57. Yvon A M, Wadsworth P, Jordan M A: Taxol suppresses dynamics of individual microtubules in living human tumor cells. Mol Biol Cell 10: 947-959, 1999.
58. Tarr M, van Helden P D: Inhibition of transcription by adriamycin is a consequence of the loss of negative superhelicity in DNA mediated by topoisomerase II. Mol Cell Biochem 93:141-146, 1990.
59. Ikemoto H, Tani E, Matsumoto T, Nakano A, Furuyama J: Apoptosis of human glioma cells in response to calphostin C, a specific protein kinase C inhibitor. J Neurosurg 83: 1008-1016, 1995.
60. Zhu D M, Narla R K, Fang W H, Chia N C, Uckun F M: Calphostin C triggers calcium-dependent apoptosis in human acute lymphoblastic leukemia cells. Clin Cancer Res 4: 2967-2976, 1998.
61. Jarvis W D, Turner A J, Povirk L F, Traylor R S, Grant S: Induction of apoptotic DNA fragmentation and cell death in HL-60 human promyelocytic leukemia cells by pharmacological inhibitors of protein kinase C. Cancer Res 54: 1707-1714, 1994.
62. Ikemoto H, Tani E, Ozaki I, Kitagawa H, Arita N: Calphostin C-mediated translocation and integration of Bax into mitochondria induces cytochrome c release before mitochondrial dysfunction. Cell Death Differ 7: 511-520, 2000.
63. LaRue J M, Stratagoules E D, Martinez J D: Deoxycholic acid-induced apoptosis is switched to necrosis by bcl-2 and calphostin C. Cancer Lett 152: 107-113, 2000.
64. Friedrich K, Wieder T, Von Haefen C, Radetzki S, Janicke R, Schulze-Osthoff K, Dorken B, Daniel P T: Overexpression of caspase-3 restores sensitivity for drug-induced apoptosis in breast cancer cell lines with acquired drug resistance. Oncogene 20: 2749-2760, 2001.
65. Janicke R U, Sprengart M L, Wati M R, Porter A G: Caspase-3 is required for DNA fragmentation and morphological changes associated with apoptosis. J Biol Chem 273: 9357-9360, 1998.
66. Janicke R U, Ng P, Sprengart M L, Porter A G: Caspase-3 is required for alpha-fodrin cleavage but dispensable for cleavage of other death substrates in apoptosis. J Biol Chem 273: 15540-15545, 1998.
67. Pollack I F, Kawecki S: The effect of calphostin C, a potent photodependent protein kinase C inhibitor, on the proliferation of glioma cells in vitro. J Neurooncol 31: 255-266, 1997.
68. Hu D E, Fan T P: Protein kinase C inhibitor calphostin C prevents cytokine-induced angiogenesis in the rat. Inflammation 19: 39-54, 1995.
69. Chen C L, Tai H L, Zhu D M, Uckun F M: Pharmacokinetic features and metabolism of calphostin C, a naturally occurring perylenequinone with antileukemic activity. Pharm Res 16: 1003-1009, 1999.
70. da Rocha A B, Mans D R, Regner A, Schwartsmann G: Targeting protein kinase C: new therapeutic opportunities against high-grade malignant gliomas? Oncologist 7: 17-33, 2002.

The invention claimed is:

1. A method of treating a subject having breast cancer which is resistant to treatment by an agent selected from the group consisting of paclitaxel and doxorubicin, the method comprising the steps of:
   administering to the subject a pharmaceutically effective dose of calphostin C; and
   activating the calphostin C.

2. The method of claim 1, wherein said breast cancer is resistant to paclitaxel.

3. The method of claim 1, wherein said breast cancer is resistant to doxorubicin.

4. The method of claim 1, wherein said cancer comprises tumor cells that have a defect in an apoptotic regulatory pathway which renders said cells resistant to chemotherapeutic treatment with taxanes or anthracyclines.

5. The method of claim 1 wherein the step of activating the calphostin C is performed by exposing a tumor-affected part of the subject to light at a suitable wavelength and intensity to activate the calphostin C.

6. The method of claim 1, wherein said cancer comprises tumor cells that have a defect in an apoptotic regulatory pathway which renders said cells resistant to chemotherapeutic treatment.

7. A method of treating a patient having breast cancer which is resistant to treatment by an agent selected from the group consisting of paclitaxel and doxorubicin, the method comprising the steps of:
   administering a pharmaceutically effective dose of calphostin C to a tumor-affected part of the subject; and
   exposing the tumor-affected part of the subject to light at a wavelength suitable for activating the calphostin C.

8. The method defined in claim 7, wherein said cancer has a p53 mutation.

9. The method of claim 7, wherein said cancer is resistant to paclitaxel.

10. The method of claim 7, wherein said cancer is resistant to doxorubicin.

11. The method of claim 7, wherein said cancer comprises tumor cells that have a defect in an apoptotic regulatory pathway which renders said cells resistant to chemotherapeutic treatment with taxanes or anthracyclines.

12. The method of claim 7, wherein the calphostin C remains substantially inactivated in other parts of the subject away from the tumor-affected part of the subject exposed to the light.

13. A method of killing breast cancer tumor cells resistant to an agent selected from the group consisting of paclitaxel and doxorubicin, the method comprising the steps of:
   administering an effective dose of calphostin C to the tumor cells; and
   activating the calphostin C to kill the tumor cells.

14. The method of claim 13, wherein said tumor cells are resistant to paclitaxel.

15. The method of claim 13, wherein said tumor cells are resistant to doxorubicin.

16. The method of claim 13, wherein said tumor cells have a defect in an apoptotic regulatory pathway which renders said cells resistant to chemotherapeutic treatment.

17. The method of claim 13, wherein the calphostin C is activated by exposing the cells to a light of suitable intensity and wavelength to activate calphostin C.

* * * * *